United States Patent [19]

Billheimer et al.

[11] Patent Number: 5,428,041
[45] Date of Patent: Jun. 27, 1995

[54] ANTIHYPERCHOLESTEROLEMIC BIS-TRIFLUOROMETHYL-SUBSTITUTED IMIDAZOLINES AND DERIVATIVES THEREOF

[75] Inventors: Jeffrey T. Billheimer; George A. Boswell, Jr.; Indawati De Lucca; Spencer Drummond, Jr., all of Wilmington; Peter J. Gillies, Hockessin, all of Del.; James M. Trzaskos, Boothwyn, Pa.

[73] Assignee: The Du Pont Merck Pharmaceutical Company, Wilmington, Del.

[21] Appl. No.: 836,323

[22] PCT Filed: May 31, 1991

[86] PCT No.: PCT/US91/03854
§ 371 Date: Mar. 4, 1992
§ 102(e) Date: Mar. 4, 1992

[87] PCT Pub. No.: WO91/19476
PCT Pub. Date: Dec. 26, 1991

[51] Int. Cl.⁶ .............. A61K 31/415; A61K 31/445; C07D 233/66; C07D 401/10

[52] U.S. Cl. .................. 514/316; 514/326; 514/386; 514/401; 514/402; 546/187; 546/210; 548/351.1; 548/352.1; 548/253; 548/254; 548/314.7; 548/325.1; 548/325.5; 548/326.5; 548/349.1; 548/350.1; 548/354.1

[58] Field of Search ............. 548/347, 351, 300, 301; 514/385, 386, 401, 326, 316; 546/210, 187

[56] References Cited

U.S. PATENT DOCUMENTS

| 4,460,598 | 7/1984 | Lautenschlager et al. | 514/398 |
| 4,623,662 | 11/1986 | DeVries | 514/585 |
| 4,651,358 | 3/1987 | Lautenschlager et al. | 514/398 |

OTHER PUBLICATIONS

Burger et al., Synthesis (1), 44-9. 1988.

*Primary Examiner*—Marianne M. Cintins
*Assistant Examiner*—Phyllis G. Spivack

[57] ABSTRACT

Provided are bis-trifluoromethyl-substituted imidazolines as inhibitors of Acyl-CoA:Cholesterol Acyltransferase (ACAT), processes for their preparation, pharmaceutical compositions, and therapeutic methods for their use as antihypercholesterolemic or antiatherosclerotic agents.

90 Claims, No Drawings

ANTIHYPERCHOLESTEROLEMIC BIS-TRIFLUOROMETHYL-SUBSTITUTED IMIDAZOLINES AND DERIVATIVES THEREOF

FIELD OF THE INVENTION

This invention relates to bis-trifluoromethyl-substituted imidazolines as inhibitors of Acyl-CoA:Cholesterol Acyltransferase (ACAT), processes for their preparation and their use as antihypercholesterolemic and antiatherosclerotic agents.

BACKGROUND OF THE INVENTION

Hypercholesterolemia, elevated blood cholesterol, is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. More important, the accumulation and storage of cholesteryl esters in the arterial wall is associated with increased activity of ACAT. Inhibition of the enzyme is expected to inhibit the formation or progression of atherosclerotic lesions in mammals by promoting reverse cholesterol transport.

There are a limited number of patents in the literature disclosing compounds that are useful as ACAT inhibitors in particular and antiatherosclerotic agents in general. For example, U.S. Pat. No. 4,623,662, issued to De Vries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 22, 1988, discloses disubstituted pyrimidineamides of oleic and linoleic acids as ACAT inhibitors useful for inhibiting intestinal absorption of cholesterol.

U.S. Pat. No. 4,460,598, issued to Lautenschläger et al. on Jul. 17, 1984, discloses 2-substituted-1,4,5-triaryl imidazoles. The synthesis and the use of these compounds in the treatment of thromboembolic, inflammatory and/or atherosclerotic diseases is disclosed.

U.S. Pat. No. 4,654,358, issued to Lautenschläger et al. on Mar. 31, 1987, discloses 2-substituted-1,4,5-triaryl imidazoles. The synthesis and the use of these compounds in the treatment of inflammatory diseases, diseases of lipid metabolism, and/or hyperlipedemic diseases is disclosed.

German Laid Open Applications No. DE 3,504,679, and German Laid Open Application No. DE 3,504,680, Lautenschläger et al., published Aug. 14, 1986, discloses 1,2,4,5-tetrasubstituted imidazoles. The synthesis and the use of these compounds in the treatment of thromboembolic, inflammatory, atherosclerotic, and lipid metabolism diseases in general is disclosed.

K. Burger, et al., *Synthesis*, 1, 44 (1988) describe an alternative synthesis of the 5-imino-2-phenyl-4,4-bis(trifluoromethyl)-4H-imidazole system. This synthesis gives rise to compounds having a 1-mesityl substituent, which is not readily removed and therefore cannot be used to synthesize compounds of this invention, which have hydrogen or methyl at the 1-position. No biological activity was disclosed.

Co-assigned applications, U.S. Ser. No. 07/279,981 and 07/416,606 filed Dec. 5, 1988 and Oct. 10, 1989, respectively, now abandoned, relate to diarylimidazoles as inhibitors of the enzyme ACAT and their use to lower serum cholesterol in mammals.

There are no known literature references disclosing the bis-trifluoromethyl-substituted imidazolines of this invention, their use as ACAT inhibitors, or their use in the treatment of atherosclerosis.

The compounds of this invention are very potent ACAT inhibitors and/or inhibitors of cholesterol biosynthesis. As shown by the data presented below in Tables 6 and 7, the compounds of this invention inhibit the ACAT enzyme with a potency equal to or better than the potency of many of the ACAT inhibitors described in the current literature. The compounds of this invention also cause a reduction in the serum cholesterol level of normolipemic (non-cholesterol fed) hamsters, whereas in general known ACAT inhibitors fail to lower serum cholesterol levels in non-cholesterol fed animals. Compounds of the invention have also been shown to inhibit cholesterol synthesis in the liver. The compounds of this invention are systemically active and are therefore expected to be useful for the treatment of atherosclerosis. The compounds of this invention have been shown to lower serum cholesterol and to have systemic ACAT inhibitory activity following oral administration, and this invention should not be construed as limited to any particular antiatherosclerotic mechanism of action.

SUMMARY OF THE INVENTION

The present invention provides novel compounds of Formula (I), processes for their preparation, pharmaceutical compositions containing bis-trifluoromethyl-substituted imidazolines and derivatives thereof, and therapeutic methods for their use as antihypercholesterolemic/antiatherosclerotic agents.

This invention provides compounds of Formula (I):

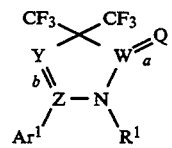

wherein $Ar^1$ is phenyl, or mono-, di-, or tri-substituted phenyl, optionally substituted with —F, —Cl, —Br, —I, —$CF_3$, —$CONH_2$, —$NO_2$, —CHO, —$CO_2Et$, —CN, —$O_2CR^9$, —$SCH_3$, —$SCF_3$, —$SO_2CF_3$, —$SO_2CH_3$, 5-tetrazolyl, —N(O)($CH_3$)$_2$, OH, $C_1$-$C_7$ alkoxy, N-piperidyl, $C_1$-$C_{10}$ alkyl, $C_3$-$C_7$ cycloalkyl, or $C_3$-$C_{10}$ substituted cycloalkyl, or $Ar^1$ may be $C_1$-$C_{10}$ alkyl, $C_3$-$C_7$ cycloalkyl, or $C_4$-$C_7$ substituted cycloalkyl substituted as above, where $R^9$ is H or alkyl, alkenyl, or alkynyl of 1 to 20 carbon atoms;

Q is O or X—$R^2$ wherein X is bonded to W, provided that when Q is O, a is a double bond;

X is N, NR$^6$, CH, or CHR$^6$, S, and R$^6$ is H, or C$_1$–C$_3$ alkyl, alkenyl, or alkynyl;

W is C or CH provided that when a is a single bond, X is NR$^6$ or CH$_2$ and W is CH, and when a is a double bond, X is N or CH and W is C;

Y is N or NR$^7$, and R$^7$ is H or C$_1$–C$_3$ alkyl;

Z is C or CH, provided that when b is a single bond, Y is NR$^7$ and Z is CH, and when b is a double bond, Y is N and Z is C; and a and b are, independently, single or double bonds;

R$^1$ is H or C$_1$–C$_3$ alkyl, alkenyl, or alkynyl;

R$^2$ is C$_4$ to C$_{15}$ alkyl, C$_4$ to C$_{15}$ alkynyl, or C$_4$ to C$_{15}$ alkenyl, which may be straight, branched or cyclic, optionally with a terminal COOH or OH group; or R$^2$ is COR$^3$ where R$^3$ is C$_1$ to C$_{15}$ alkyl, C$_2$ to C$_{15}$ akynyl, or C$_2$ to C$_{15}$ alkenyl, which may be straight, branched, or cyclic, optionally with a terminal COOH or OH group; or R$^2$ is COAr$^2$, CH$_2$Ar$^2$, CO$_2$Ar$^2$, CONR$^8$Ar$^2$, where R$^8$ is H or C$_1$–C$_3$ alkyl, SO$_2$Ar$^2$, SO$_2$NHAr$^2$, or SO$_2$R$^3$;

Ar$^2$ is phenyl or substituted phenyl, optionally substituted with one or more of —F, —Cl, —Br, —I, —CF$_3$, p—NO$_2$, —CN, —CHO, —N$_3$, C$_1$–C$_7$ alkyl, C$_1$–C$_7$ alkoxy, phenyl, or NR$^4$R$^5$, where R$^4$ and R$^5$ are independently H, or C$_1$–C$_3$ alkyl, or together represent a carbocyclic ring of 3–5 carbons, or Ar$^2$ is C$_2$–C$_{11}$, saturated, unsaturated, or aromatic, and which may be straight, branched, or cyclic; or N-morpholyl; 2- or 3-thiophyl; 2- or 3-pyrrolyl; or 2- or 3-furyl;

Provided that: when X is CH or CH$_2$ and R$^2$ is COAr$^2$, Ar$^1$ and Ar$^2$ are independently, phenyl or substituted phenyl, and when X is CH$_2$, R$^2$ is COAr$^2$, CH$_2$Ar$^2$, or CO$_2$Ar$^2$; or a resolved optical antipode of any chiral form thereof; or a pharmaceutically acceptable salt thereof.

Preferred are compounds of Formula (I) above wherein:

Ar$^1$ is phenyl, or mono-, di-, or tri-substituted phenyl, optionally substituted with —F, —Cl, —Br, —I, —CN, —CF$_3$, —CONH$_2$, —OH, —NO$_2$, 5-tetrazolyl, C$_1$–C$_7$ alkoxy, N-piperidyl, —O$_2$CR$^9$, where R$^9$ is C$_1$–C$_{20}$ alkyl, alkenyl, or alkynyl, C$_1$–C$_{10}$ alkyl, C$_3$–C$_7$ cycloalkyl, or C$_3$–C$_{10}$ substituted cycloalkyl, or Ar$^1$ is cyclohexyl;

Q is O or X—R$^2$ wherein X is bonded to W, provided that when Q is O, a is a double bond;

X is N, NR$^6$, CH, or CHR$^6$, S, and R$^6$ is H, or C$_1$–C$_3$ alkyl, alkenyl, or alkynyl;

W is C or CH, provided that when a is a single bond, X is NR$^6$ or CH$_2$ and W is CH, and when a is a double bond, X is N or CH and W is C;

Y is N or NR$^7$, and R$^7$ is H or CH$_3$;

Z is C or CH, provided that when b is a single bond, Y is NR$^7$ and Z is CH, and when b is a double bond, Y is N and Z is C; and a and b are, independently, single or double bonds;

R$^1$ is H or C$_1$–C$_3$ alkyl, alkenyl, or alkynyl;

R$^2$ is COAr$^2$, CH$_2$Ar$^2$, CO$_2$Ar$^2$, or CONR$^8$Ar$^2$, wherein R$^8$ is H or C$_1$–C$_3$ alkyl; and Ar$^2$ is phenyl, or substituted phenyl, optionally substituted with one or more of —F, —Cl, —Br, —I, —CF$_3$, —N$_3$, phenyl, C$_1$–C$_7$ alkyl, C$_1$–C$_7$ alkoxy, p—NO$_2$, —CHO, —CN, or NR$^4$R$^5$ where R$^4$ and R$^5$ are independently H, or C$_1$–C$_3$ alkyl, or together represent a carbocyclic ring of 3–5 carbon atoms, or Ar$^2$ is C$_3$–C$_{11}$, saturated, unsaturated, or aromatic, and which may be straight, branched, or cyclic; or N-morpholyl; 2- or 3-thiophyl; 2- or 3-pyrrolyl; or 2- or 3- furyl.

More preferred are compounds of Formula (I) above wherein:

Ar$^1$ is phenyl, or monosubstituted phenyl, substituted with —F, —Cl, —Br, —CN, —CF$_3$, —OH, C$_1$–C$_7$ alkoxy, —NO$_2$, —CONH$_2$, N-piperidyl, CH$_3$ or —O$_2$CR$^9$ where R$^9$ is C$_1$–C$_{20}$ alkyl, alkenyl, or alkynyl or Ar$^1$ is cyclohexyl;

Q is X—R$^2$ wherein X is bonded to W;

X is NR$^6$ or CH$_2$, and R$^6$ is H, or C$_1$–C$_3$ alkyl, alkenyl, or alkynyl;

W is CH;

Y is N;

Z is C;

R$^1$ is H, CH$_3$, or C$_2$H$_5$; and

R$^2$ is COAr$^2$ or CONR$^8$Ar$^2$, wherein R$^8$ is H or C$_1$–C$_3$ alkyl; and Ar$^2$ is monosubstituted phenyl, optionally substituted with —F, —Cl, —Br, —CN, —CF$_3$, C$_1$–C$_7$ alkyl, C$_1$–C$_4$ alkoxy, p-NO$_2$, phenyl, N-piperidyl, or dimethylamino, or Ar$^2$ is saturated C$_6$–C$_{11}$, which may be straight or branched.

Even more preferred are compounds of Formula (I) above wherein:

Ar$^1$ is phenyl, or monosubstituted phenyl, p-substituted with —F, —Cl, —Br, —CN, —OH, —OCH$_3$, N-piperidyl, —CONH$_2$, or O$_2$CR$^9$ where R$^9$ is C$_1$–C$_{20}$ alkyl, alkenyl or alkynyl;

Q is X—R$^2$ wherein X is bonded to W;

X is NR$^6$ or CH$_2$, and R$^6$ is H or C$_1$–C$_3$ alkyl, alkenyl, or alkynyl;

W is CH;

Y is N;

Z is C;

R$^1$ is CH$_3$;

R$^2$ is COAr$^2$ or CONR$^8$Ar$^2$, wherein R$^8$ is H or C$_1$—C$_3$ alkyl; and Ar$^2$ is monosubstituted phenyl, p-substituted with —F, —Cl, phenyl, C$_1$–C$_4$ alkyl, p-NO$_2$, N-piperidyl, C$_1$–C$_4$ alkoxy, —CN, or Ar$^2$ is saturated C$_6$–C$_{11}$, which may be straight or branched.

Specifically preferred are the compounds of the formula shown below wherein:

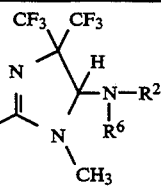
| | | | |
|---|---|---|---|
| a) (Ex. 11) | $R^{10}$ = F, | $R^6$ = $CH_3$, | 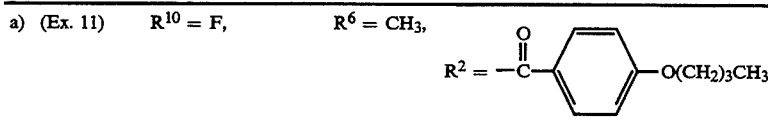 |
| b) (Ex. 13) | $R^{10}$ = F, | $R^6$ = $CH_3$, | 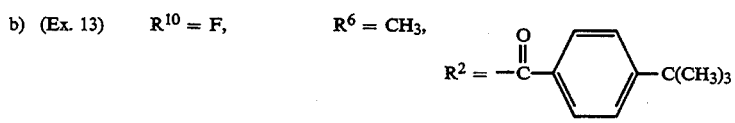 |
| c) (Ex. 14) | $R^{10}$ = F, | $R^6$ = $CH_3$, | 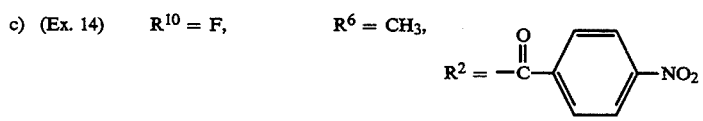 |
| d) (Ex. 31) | $R^{10}$ = F, | $R^6$ = H, | 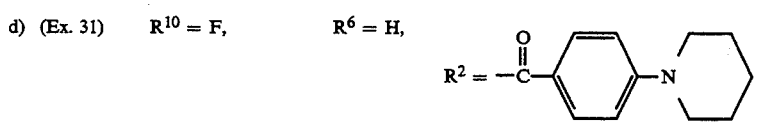 |
| e) (Ex. 10A) | $R^{10}$ = F, | $R^6$ = $CH_3$, | 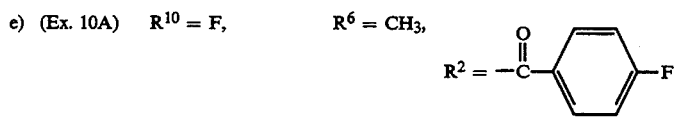 |
| f) (Ex. 32) | 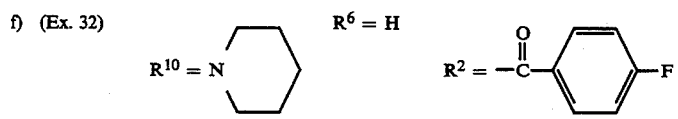 | $R^6$ = H |  |
| g) (Ex. 16) | $R^{10}$ = F, | $R^6$ = $CH_3$ | $R^2$ = $COC_6H_{13}$ |
| h) (Ex. 30) | $R^{10}$ = F, | $R^6$ = H | 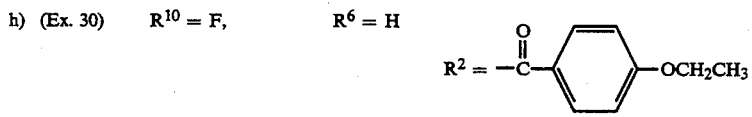 |
| i) (Ex. 12) | $R^{10}$ = F, | $R^6$ = $CH_3$ | 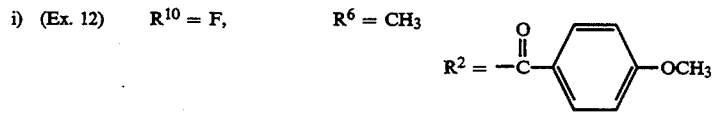 |
| j) (Ex. 15) | $R^{10}$ = F, | $R^6$ = $CH_3$ | 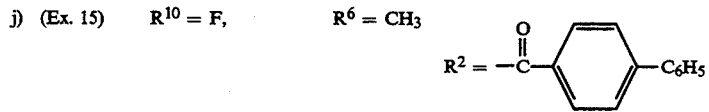 |
| k) (Ex. 28) | $R^{10}$ = F, | $R^6$ = $CH_3$ | 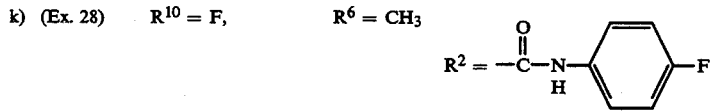 |
| l) (Ex. 33) | 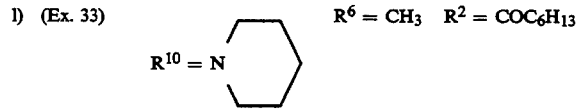 | $R^6$ = $CH_3$ | $R^2$ = $COC_6H_{13}$ |
| m) (Ex. 34) | $R^{10}$ = $CH_3O$, | $R^6$ = $CH_3$ | $R^2$ = $CO(CH_2)_3CH(CH_3)_2$ |

-continued

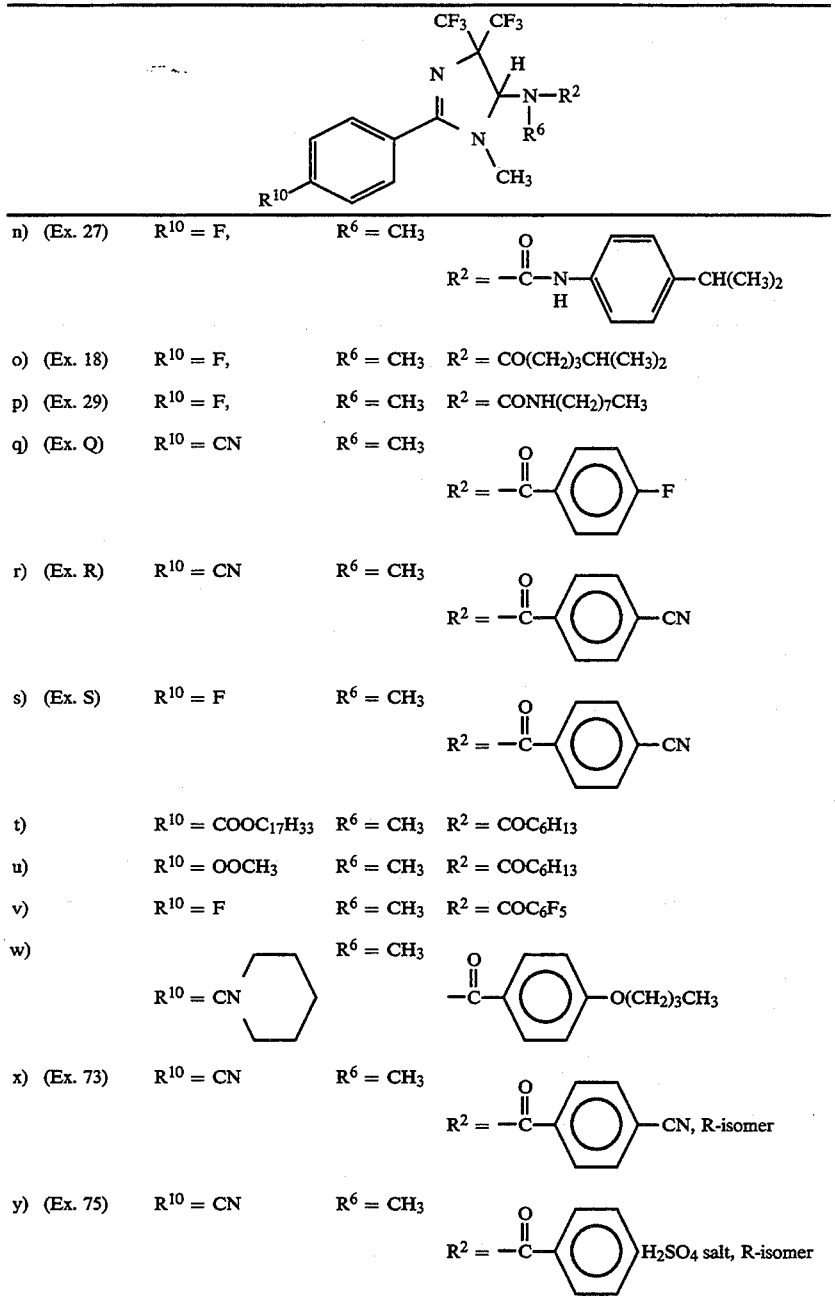

| | | | |
|---|---|---|---|
| n) (Ex. 27) | $R^{10}$ = F, | $R^6$ = $CH_3$ | $R^2 = -\overset{O}{\underset{}{C}}-\underset{H}{N}-\text{C}_6\text{H}_4-CH(CH_3)_2$ |
| o) (Ex. 18) | $R^{10}$ = F, | $R^6$ = $CH_3$ | $R^2$ = $CO(CH_2)_3CH(CH_3)_2$ |
| p) (Ex. 29) | $R^{10}$ = F, | $R^6$ = $CH_3$ | $R^2$ = $CONH(CH_2)_7CH_3$ |
| q) (Ex. Q) | $R^{10}$ = CN | $R^6$ = $CH_3$ | $R^2 = -\overset{O}{\underset{}{C}}-\text{C}_6\text{H}_4-F$ |
| r) (Ex. R) | $R^{10}$ = CN | $R^6$ = $CH_3$ | $R^2 = -\overset{O}{\underset{}{C}}-\text{C}_6\text{H}_4-CN$ |
| s) (Ex. S) | $R^{10}$ = F | $R^6$ = $CH_3$ | $R^2 = -\overset{O}{\underset{}{C}}-\text{C}_6\text{H}_4-CN$ |
| t) | $R^{10}$ = $COOC_{17}H_{33}$ | $R^6$ = $CH_3$ | $R^2$ = $COC_6H_{13}$ |
| u) | $R^{10}$ = $OOCH_3$ | $R^6$ = $CH_3$ | $R^2$ = $COC_6H_{13}$ |
| v) | $R^{10}$ = F | $R^6$ = $CH_3$ | $R^2$ = $COC_6F_5$ |
| w) | $R^{10}$ = CN-piperidinyl | $R^6$ = $CH_3$ | $-\overset{O}{\underset{}{C}}-\text{C}_6\text{H}_4-O(CH_2)_3CH_3$ |
| x) (Ex. 73) | $R^{10}$ = CN | $R^6$ = $CH_3$ | $R^2 = -\overset{O}{\underset{}{C}}-\text{C}_6\text{H}_4-CN$, R-isomer |
| y) (Ex. 75) | $R^{10}$ = CN | $R^6$ = $CH_3$ | $R^2 = -\overset{O}{\underset{}{C}}-\text{C}_6\text{H}_4-$ $H_2SO_4$ salt, R-isomer |

Also specifically preferred are the compounds: 1-(4-cyanophenyl)-2-[2-(4-fluorophenyl)-4,5-dihydro-1-methyl-4,4-bis(trifluoromethyl)-1H-imidazol-5-yl]-ethanone; 1-(4-fluorophenyl)-2-[2-(4-fluorophenyl)-4,5-dihydro-1-methyl-4,4-bis(trifluoromethyl)-1H-imidazol-5-yl]-ethanone; and 1-(4-fluorophenyl)-2-[2-(4-fluorophenyl)-4,5-dihydro-1-ethyl-4,4-bis(trifluoromethyl)-1H-imidazol-5-yl]-ethanone.

DETAILED DESCRIPTION OF THE INVENTION

Synthesis

The novel compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the imidazoline and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternative methods described must then be used.

The compounds of Formula (I) wherein X is N, W is C, Z is C, Y is N, $R^2$ is $COAr^2$, $Ar^1$ is phenyl or substituted phenyl, and $R^1$ is H or $CH_3$ can be prepared by the route shown in Scheme 1. The requisite 2-hexafluoroisopropylamino-4,5-diarylimidazoles (1) are prepared as described in U.S. Pat. No. 4,348,404, the teaching of which is hereby incorporated by reference.

Treatment of the 2-hexafluoroisopropylamino-4,5-diarylimidazole (1, $R^1$=H or $CH_3$) with excess peracid such as m-chloroperbenzoic acid (MCPBA), preferably 3 or more equivalents in 2 or more portions in refluxing chloroform for 2 hours, gives the corresponding N-[(4,4-bis(trifluoromethyl)-4,5-dihydro-2-aryl-1-methyl-1H-imidazol-5-ylidene)]-benzamide (2, $R^1$=H or $CH_3$). Alternatively, monoperoxyphthalic acid magnesium salt (MMPP) in glacial acetic acid may be used instead of MCPBA in chloroform in the conversion of the 2-hexafluoroisopropylamino-4,5-diarylimidazoles (1) to the bis-trifluoromethyl substituted imidazolines (2).

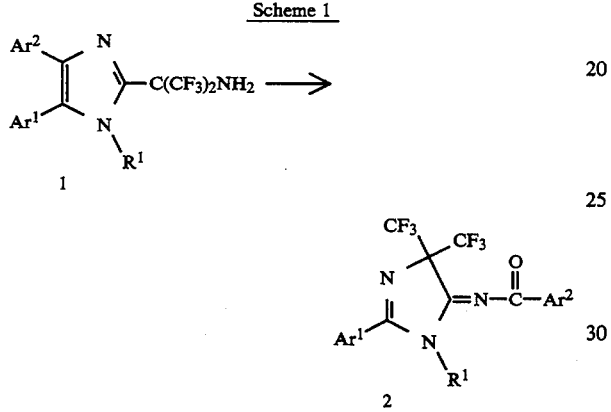

Alternatively, oxidation of 2-hexafluoroisopropylamino-4,5-diarylimidazoles (1) with singlet oxygen generated by irradiating oxygen with a Tungsten lamp (400 watt) in the presence of a catalytic amount of methylene blue in chloroform and methanol (1:1) followed by acid treatment gives the bis-trifluoromethyl substituted imidazolines (2), as shown in Scheme 1.1.

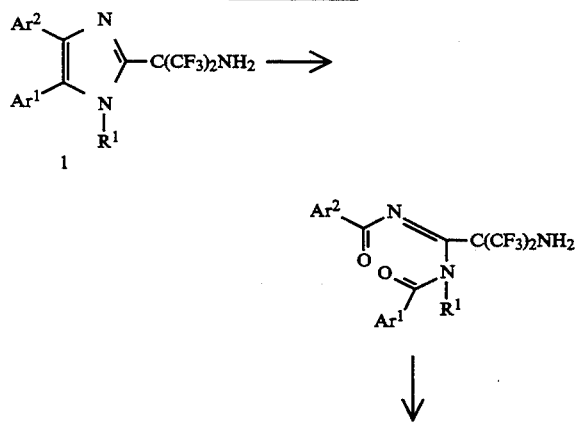

The compounds of Formula (I) wherein X is NH, Y is N, W is CH, Z is C, $R^2$ is $COAr^2$, and a is a single bond and b is a double bond can be prepared by the route shown in Scheme 2. The benzamides of Formula (3) can be prepared by reducing the requisite imines of Formula (2) with lithium aluminum hydride (preferably, 2 equivalents) in tetrahydrofuran at room temperature for 1 to 24 hours or sodium borohydride (preferably 1.1 equivalents) in refluxing ethanol. Lithium aluminum hydride is the preferred reducing agent because reduction with sodium borohydride gives rise to a mixture of 3 and the ring reduction product of 4. Other hydride-type reducing reagents such as lithium aluminum tri-tertiary-butoxyhydride may also be used.

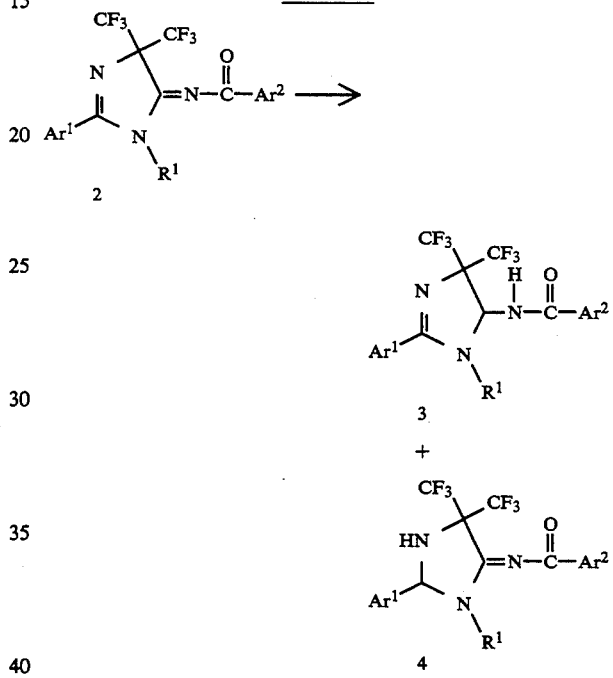

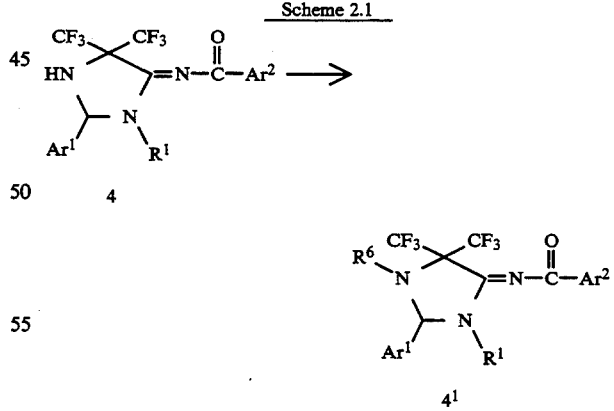

The ring reduction product 4, can be converted to the corresponding alkali metal salt by the addition of a base such as sodium hydride, and the salt is alkylated with methyl iodide in a polar solvent such as dimethyl formamide at room temperature to give compound $4^1$ (Scheme 2.1)

The amides, carbamates and ureas of Formula (I) wherein $R^2$ is as defined above can be prepared by the route shown in Scheme 3. The requisite benzamide of Formula (3) is converted to the corresponding alkali metal salt by the addition of a base such as sodium hydride, and the salt is alkylated with methyl iodide in a polar solvent such as dimethylformamide at room temperature. The N-methyl benzamides of Formula (5) can be cleaved to the N-methyl aminals of Formula (6) by the route shown in Scheme 3. Treatment of the requisite N-methyl benzamide with potassium tert-butoxide (6 equivalents) and water (2equivalents) in ether at room temperature gives the corresponding N-methyl aminals of Formula (6), which can be converted into the hydrochloride salt with hydrochloric acid in ether. The amides, ureas and carbamates of Formula (7) are prepared by coupling the aminals of Formula (6) with an acyl chloride, isocyanate or chloroformate by the route shown in Scheme 3. Alternatively, other literature methods for forming amide bonds may be employed which involve reaction of carboxylic acids and amines.

One method for amide bound formation is to use a coupling reagent which generates a reactive intermediate such as a mixed anhydride or active ester. Examples of such coupling agents are disubstituted carbodiimides, N,N'-carbonyldiimidazole, diphenylphosphoryl azide, and the like. For example, the coupling can be carried out with a disubstituted carbodiimide such as dicyclohexylcarbodiimide in an appropriate solvent such as methylene chloride, acetonitrile, toluene, or dimethylformamide. Nucleophilic hydroxy compounds such as 1-hydroxy-1H-benzotriazole, which form highly active esters, may be added to catalyze the reaction.

Reaction of the requisite aminal (6) with the appropriate acyl or aroyl chloride in pyridine and methylene chloride at room temperature gives the corresponding amides of Formula (7). Similarly, reaction of the aminal with alkyl or aryl isocyanates in methylene chloride at room temperature gives the corresponding ureas of Formula (7). The carbamates of Formula (7) are prepared by allowing the requisite N-methyl aminal of Formula (6) to react with alkyl or aryl chloroformates in methylene chloride at room temperature to the reflux temperature of the solvent.

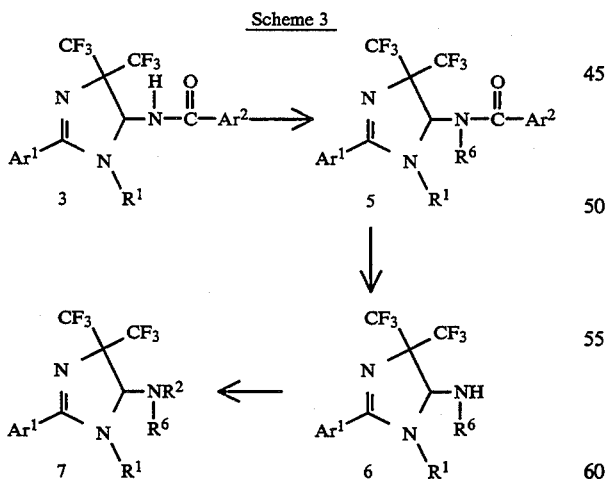

Scheme 3

The benzamides of Formula (7) having different para-substituents on the benzamide group and the pendant phenyl group are prepared by the route shown in Scheme 4. By starting with o-fluorophenyl analogs, which can be prepared according to Scheme 1 wherein $Ar^1=Ar^2=$o-fluoro-phenyl, ortho substituted analogs can be prepared by aromatic nucleophilic substitution as shown in Scheme 4. Compounds wherein $Ar^2$ may be ortho, meta, and/or para substituted may be prepared using Scheme 3 by reacting compound (6) with the appropriate mono-, di-, or trisubstituted (any combinations at any positions) benzoyl chloride, to yield the desired compounds of Formula (7). Treatment of the requisite benzamide of Formula (8) with the appropriate nucleophile, e.g., cyanide, ethoxide, or piperidine, in a polar solvent such as dimethyl sulfoxide (DMSO) at a temperature from room temperature to the boiling point of the solvent gives the benzamides of Formulas (9), (10) and (11), which may be separated by conventional means such as crystallization, high pressure liquid chromatography (HPLC), conventional column chromatography and other procedures known to those skilled in the art.

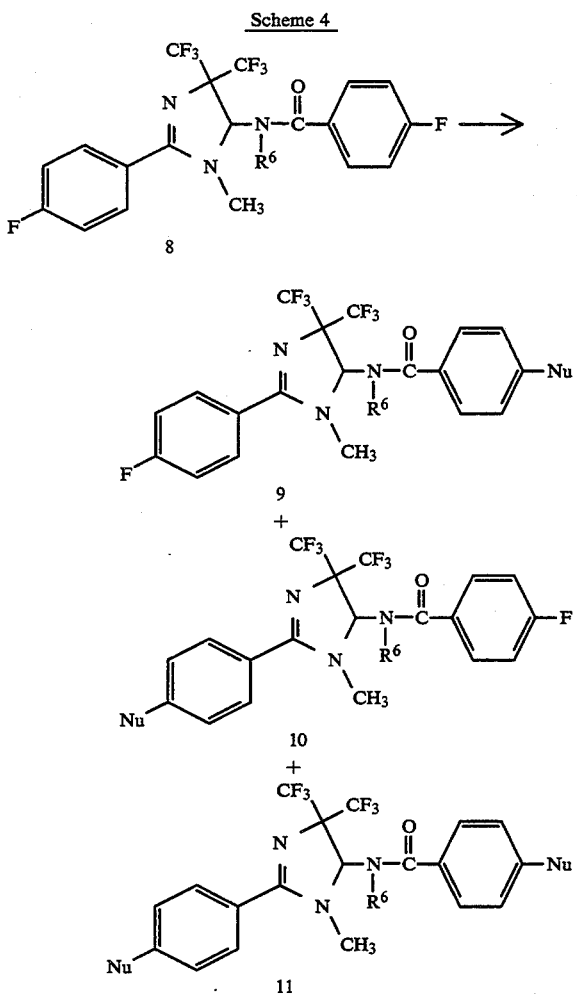

As an alternative, the amides of Formula (13) wherein $R^2$ is $COR^3$, where $R^3$ is $C_1$ to $C_{15}$ alkyl, $C_2$ to $C_{15}$ alkenyl, or $C_2$ to $C_{15}$ alkynyl, with a terminal $CO_2H$ or OH group, may be prepared according to the route shown in Scheme 5. Treatment of the requisite amide of Formula (12) with the desired nucleophile, e.g., methoxide, piperidine, etc., gives the corresponding amide of Formula (13) wherein the para-fluorine of the pendant phenyl group has been replaced by the new group.

Scheme 5

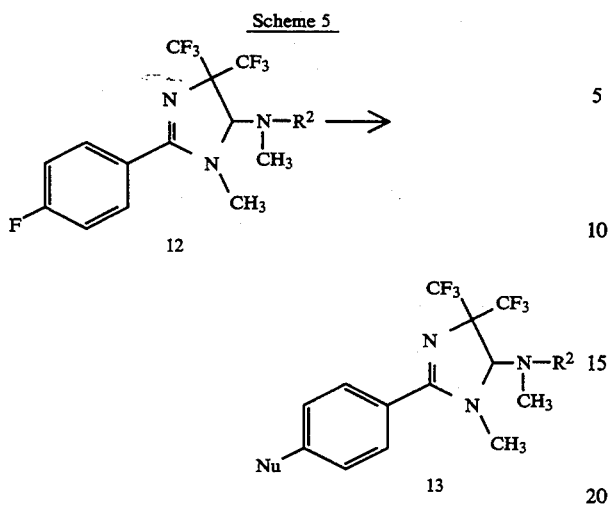

The bis-trifluoromethyl substituted imidazolines of Formula (16) are prepared by the route shown in Scheme 6. The requisite 2-hexafluoroisopropylamino-4,5-diarylpyrroles of Formula (14), are prepared according to the method of U.S. Pat. No .4,335,136, the teaching of which is hereby incorporated by reference. These compounds of Formula (14) are oxidized with singlet oxygen (see Scheme 6.1 below) as described above for Scheme 1.1. Alternatively, compounds of Formula (14) are allowed to react with excess MCPBA as described above for Scheme 1 to give the bis-trifluoromethyl substituted imidazoles of Formula (16) and the novel hydroxypyrrolinene of Formula (15), which can be separated by chromatography or other means known to those skilled in the art. The alkylated derivatives of Formula (17) are made by converting the requisite imidazoline of Formula (16) into the corresponding alkali metal salt by addition of a base such as sodium hydride, and the salt is alkylated with methyl iodide in a polar solvent such as dimethylformamide at temperatures from room temperature to the reflux temperature of the solvent.

Scheme 6.1

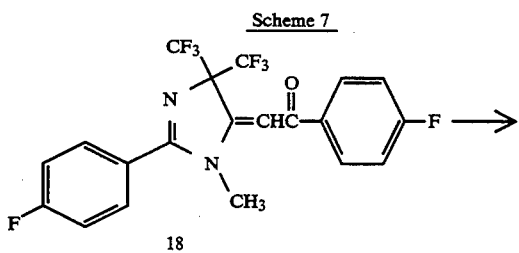

The imidazoles of Formula (17.1) can be prepared by reducing the imidazoles of Formula (17) with zinc dust in refluxing acetic acid, as shown in Scheme 7.1.

The imidazoles of Formula (17 or 17.1) having different para-substituents on the phenyl ketone and the pendant phenyl group are prepared by the route shown in Scheme 7. Compounds having ortho and/or meta substituted phenyl groups can be prepared by starting with compound (14) having appropriately substituted $Ar^1$ and $Ar^2$ groups. Treatment of the requisite imidazole of Formula (18) with the appropriate nucleophile in a polar solvent such as dimethyl sulfoxide (DMSO) at a temperature from room temperature to the boiling of the solvent gives the imidazoles of Formulas (19), (20), and (21) which may be separated by conventional means such as crystallization, high pressure liquid chromatography (HPLC), conventional column chromatography and other procedures known to those skilled in the art.

Scheme 7

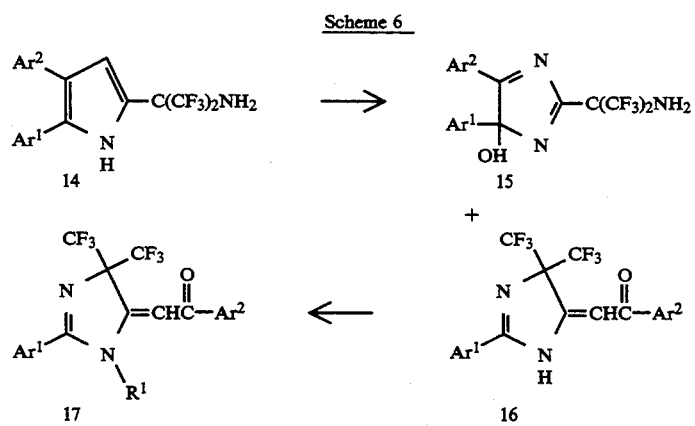

Scheme 7

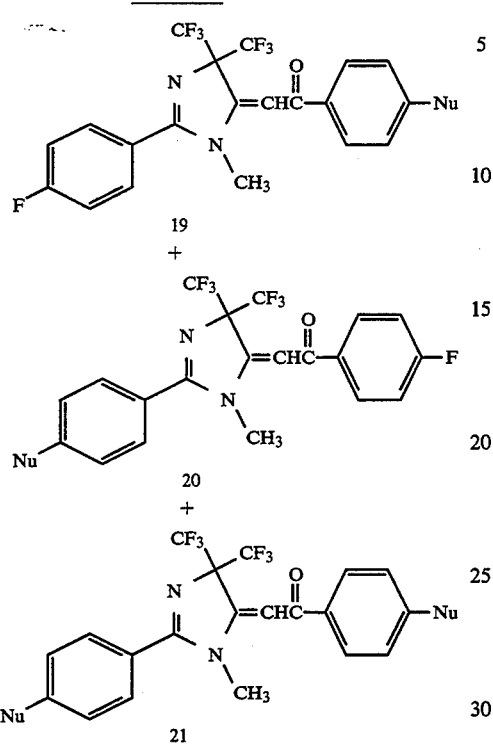

Scheme 7.1

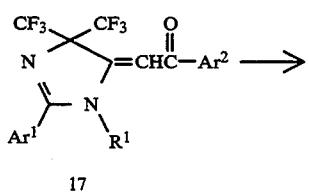

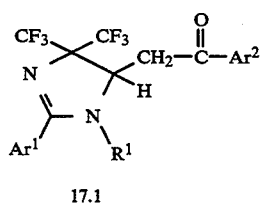

The carbamates of Formula (22) wherein the para-substituent of $Ar^2$ is an electron-donating group such as alkoxide or alkyl are prepared as shown in Scheme 8. Allowing the requisite 2-hexafluoroisopropylamino-4,5-diarylimidazole of Formula (1) to react with excess MCPBA as described in Scheme 1 gives either the corresponding carbamates of Formula (22) or a mixture of the carbamates of Formula (22) and benzamides of Formula (2) depending on the reaction time, degree of excess MCPBA, and the electron-donating ability of the para-substituents.

Scheme 8

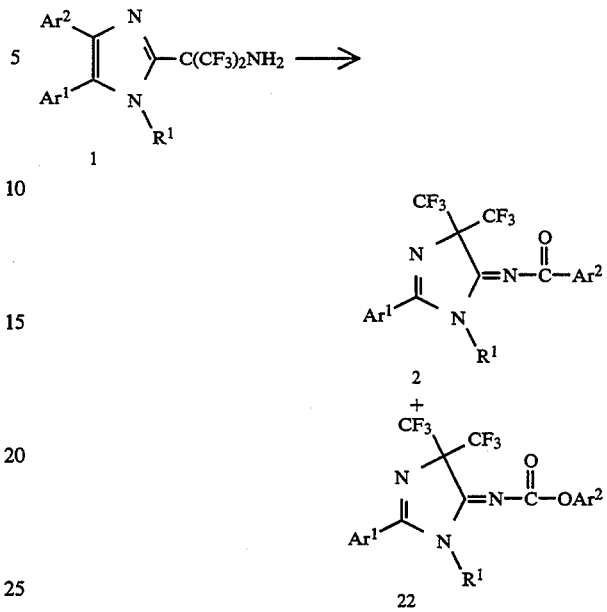

The carbamates of Formula (24, $R^2=CO_2Ar^2$), the benzamides of Formula (24, $R^2=COAr^2$), and the ureas of Formula (24, $R^2=CONHAr^2$) can also be prepared as shown in Scheme 9. Treatment of the requisite benzoyl imine of Formula (2) with ammonium hydroxide or ammonia in methanol at room temperature to the temperature of the refluxing solvent for 1 to 48 hours, or with a strong acid such as concentrated sulfuric acid at room temperature for 10–15 minutes, affords the amidine of Formula (23). Other solvents known to those skilled in the art that are compatible with the reactants and products can be used in place of methanol. The benzamides, ureas, and carbamates of Formula (24) wherein $R^2$ is $COAr^2$, $CONHAr^2$, or $CO_2Ar^2$ and $Ar^2$ is different from the $Ar^1$ of the benzamide of Formula (2), are prepared by reacting the requisite amidine of Formula (24) with a compound of the formula $ClCOAr^2$, $ClCONHAr^2$, $ClCONHR^3$, $ClCOR^3$, $O=C'N-Ar^2$, or $O=C=N-R^3$ in a polar solvent such as pyridine or benzene with dimethylaminopyridine.

Scheme 9

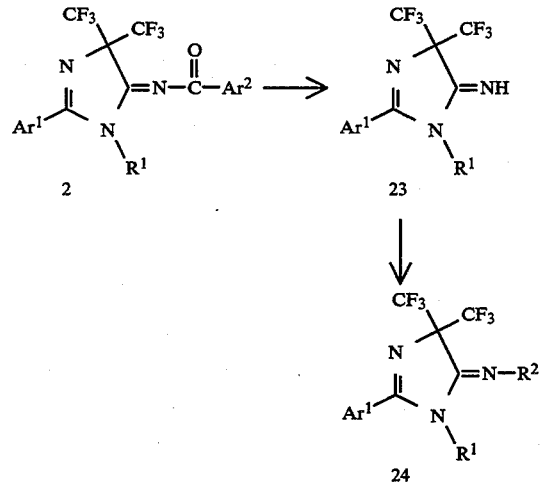

An alternative synthesis of the benzoyl imines of Formula (2) of Scheme 1 wherein $Ar^1$ is different from $Ar^2$ or $Ar^1$ is alkyl, cycloalkyl or substituted cycloalkyl, is shown in Scheme 10. Acylation of the requisite 2-hexafluoroisopropylamino-4,5-diarylimidazole of Formula (1), wherein $R^1$ is $CH_3$ or H, in refluxing benzene for 4 days, or neat for 4 hours at 150° or acid chloride and pyridine at 120°, with the appropriate acid chloride, $R^{11}COCl$, wherein $R^{11}$ can be $Ar^1$, $C_3$ to $C_{10}$ alkyl, $C_3$ to $C_7$ cycloalkyl, or $C_3$ to $C_7$ substituted cycloalkyl, gives the corresponding bicyclic derivatives of Formula (25). Compounds wherein $Ar^1$ is ortho, meta, and/or para substituted phenyl can be prepared using Scheme 10, wherein compound (1) is reacted with an acid chloride, $R^{11}COCl$, wherein $R^{11}$ is a mono-, di-, and/or trisubstituted phenyl (any combinations at any positions). Or $R^{11}$ may be heteroaromatic, or aliphatic (straight chain, branched, cycloalkyl), which may have additional substitutions, e.g.,

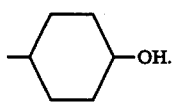

Higher boiling solvents such as toluene, xylenes, or chlorobenzenes can be employed to accelerate the reaction. The requisite bicyclic derivative of Formula (25) is allowed to react with excess MCPBA in refluxing chloroform to give the bis-trifluoromethyl substituted imidazoline of Formula (26), which loses the $Ar^1CO$ substituent on nitrogen during the workup to afford (27). The N-substituted bis-trifluoromethyl substituted imidazolines of Formula (28) can be synthesized by converting the requisite benzamide of Formula (27) into the corresponding alkali metal salt by the addition of a base such as sodium hydride, and the resultant salt is alkylated with methyl iodide in a polar solvent such as dimethylformamide.

Scheme 10

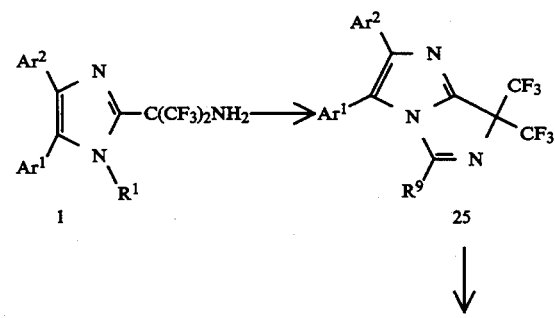

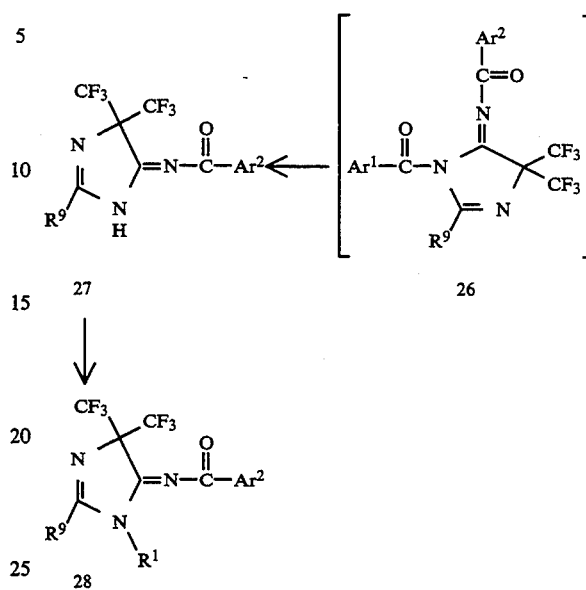

The imidazolinones of Formula (29) are prepared as shown in Scheme 11. Exposure of the requisite benzoyl imine of Formula (2) (Scheme 1) to chromatographic grade basic alumina (Activity II–IV) in ether at room temperature to the temperature of the refluxing solvent for 1 to 48 hours gives rise to the corresponding imidazoline-2-ones of Formula (29). Other solvents such as tetrahydrofuran may be used.

Scheme 11

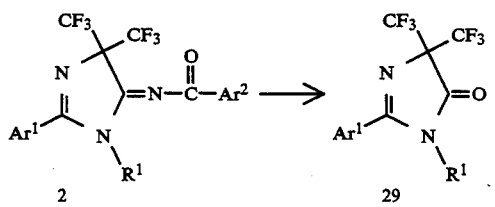

Preparation of pharmaceutically suitable salts of Formula (i) can be done in accordance with well known techniques of forming salts. Physiologically acceptable salts include but are not limited to acid addition salts, such as the hydrochloric, sulfuric, acetic, trifluoroacetic, succinic, citric, and benzenesulfonic acid salts.

The compounds of this application that have a chiral center may be resolved into the pure or partially pure optical isomers by any of the appropriate procedures known to those skilled in the art.

The compounds of this invention and their preparation can be further understood by the following examples, which do not constitute a limitation of the invention. In these examples, unless otherwise indicated, all temperatures are in degrees centigrade and parts and percentages are by weight.

EXAMPLE 2

Preparation of
N-[4,4-bis(trifluoromethyl)-2-(4-fluorophenyl)-4,5-dihydro-1-methyl-1H-imidazol-5-ylidene]-4-fluoro-benzamide

Method A

To a solution of α,α-bis(trifluoromethyl)-4,5-bis(4-fluorophenyl)-1-methyl-1H-imidazole-2-methanamine (36.0 g, 0.076 mole) in chloroform (1.8 L) was added portionwise, m-chloroperbenzoic acid (MCPBA, 26.1 g, 0.152 mole). The reaction mixture was refluxed under nitrogen for one hour. Then additional MCPBA (13.0 g, 0.076 mole) was added and the mixture was refluxed for 1 hour. The solution was cooled to room temperature and poured into saturated sodium bicarbonate (1 L). The organic layer was washed successively with saturated sodium bicarbonate solution, 10% sodium sulfite solution, water, and saturated sodium chloride solution, dried over magnesium sulfate and evaporated under vacuum. The residue was triturated with hexane to give the title compound (23.2 g, 68%) as an off-white solid. An analytical sample was prepared by recrystallization from methanol-hexane to give a white solid: mp 112°–113°; HRMS m/e calcd for $C_{19}H_{11}N_3OF_8$ (M+) 449.0774, found 449.0770; $^1$H NMR (CDCl$_3$/TMS) δ 3.13(s,3H,NCH$_3$), 7.13–7.30(m,4H,H$_{arom}$), 7.73(q,2H,H$_{arom}$), 8.06(q,2H,H$_{arom}$). Analysis Calcd for $C_{19}H_{11}N_3OF_8$: C,50.79; H,2.47; N,9.35. Found: C,50.81; H,2.72; N,9.10.

Method B

To a solution of α,α-bis(trifluoromethyl)-4,5-bis(4-fluorophenyl)-1-methyl-1H-imidazole-2-methanamine (17.6 g, 0.04 mole) in chloroform (1.25 L) was added portionwise, m-chloroperbenzoic acid (MCPBA, 17.2 g, 0.10 mole). The reaction mixture was refluxed under nitrogen for one hour, cooled to room temperature and poured into 10% sodium bicarbonate (1 L). The organic layer was washed successively with 10% sodium bicarbonate solution, 10% sodium sulfite solution, water, and saturated sodium chloride solution, dried over magnesium sulfate and evaporated under vacuum. The residue was triturated with hexane to give the title compound (8.8 g, 50%) as a white solid: mp 109°–114°; $^1$H NMR (CDCl$_3$/TMS) δ 3.13(s,3H,NCH$_3$), 7.13–7.30(m,4H,H$_{arom}$), 7.73(q,2H,H$_{arom}$), 8.06(q,2H,H$_{arom}$).

Method C

To a solution of α,α-bis(trifluoromethyl)-4,5-bis(4-fluorophenyl)-1-methyl-1H-imidazole-2-methanamine (0.24 g, 0.5 mmole) in acetic acid (10 mL) was added portionwise, monoperoxyphthalic acid magnesium salt (MMPP, 0.30 g, 1.0 mmole). The reaction mixture was stirred under nitrogen overnight. Then additional MMPP (0.15 g, 0.5 mmole) was added and the mixture was heated at 112° for 4 hours. The solution was cooled to room temperature and poured into water. The organic layer was washed successively with saturated sodium bicarbonate solution, 10% sodium sulfide solution, water, and saturated sodium chloride solution, dried over magnesium sulfate and evaporated under vacuum. The residue was triturated with hexane to give the title compound (0.60 g, 25%) as a yellow solid: $^1$H NMR (CDCl$_3$/TMS) δ 3.13 (s,3H,NCH3), 7.13–7.30(m,4H,H$_{arom}$), 7.73(q,2H,H$_{arom}$), 8.06(q,2H,H$_{arom}$).

Method D

To a solution of α,α-bis(trifluoromethyl)-4,5-bis(4-fluorophenyl)-1-methyl-1H-imidazole-2-methanamine (0.5 g, 1.1 mole) in methanol (1.5 l) was added methylene blue (10 mg). Oxygen gas or air was bubbled through the solution while irradiating with a Tungsten lamp (400 watt) for 8 hours. 1M hydrochloric acid in ether (10 ml) was added to the reaction mixture and stirred for 1 hour at room temperature. The mixture was treated with saturated sodium carbonate solution (15 ml) and then concentrated in vacuo. The concentrate was resuspended in ethyl acetate (200 ml) and water (50 ml). The organic layer was washed with saturated ammonium chloride and sodium chloride solution, dried over sodium sulfate (anhyd.) and evaporated under vacuum. The residue was purified by column chromatography, eluting with hexane-ethyl acetate (10:1) to give the title compound (312 mg, 61%).

EXAMPLE 5

N-[4,4-bis(trifluoromethyl)-2-(4-methylphenyl)-4,5-dihydro-1H-imidazol-5-ylidene]-4-methylbenzamide To a solution of α,α-bis(trifluoromethyl)-4,5-bis(4-methylphenyl)-1-methyl-1H-imidazol-2-methanamine (1.0 g, 2.3 mmole) in chloroform (10 mL) was added portionwise, m-chloroperbenzoic acid (0.40 g, 2.3 mmole). The reaction mixture was refluxed under nitrogen for two hours. The solution was cooled to room temperature and poured into saturated sodium bicarbonate (100 mL). The organic layer was washed successively with saturated sodium bicarbonate solution, 10% sodium sulfite solution, water, and saturated sodium chloride solution, dried over magnesium sulfate and evaporated under vacuum. The residue (75% benzamide and 25% ester analyzed by HPLC with a (DL)-phenylglycine column eluted with 10% isopropanol-hexane) was purified by HPLC on a silica sorbax column which was eluted with dichloromethane to give the title compound (40 mg, 4%) as a semisolid: MS m/e 442 (M+ +H); $^1$H NMR (CDCl$_3$/TMS) δ 3.00(s,6H,CH$_3$), 3.13(s,3H,NCH$_3$), 7.27–7.37(m,4H,H$_{arom}$), 7.57(d,J=7 Hz,2H,H$_{arom}$), 7.90(d,J=7 Hz,2H,H$_{arom}$).

The compounds of Examples 2 and 5, and other compounds of Formula (I) wherein a is a double bond which have been prepared or which could be prepared using the same or similar synthetic methods, are listed in Table 1. The additional compounds listed in Table 1 were prepared according to the procedure of Example 2, Method B. The yields may be improved by using the procedure of Example 2, Method A. Alternative peracids such as monoperoxyphthalic acid magnesium salt (MMPP) can be used as shown in Example 2, Method C.

TABLE 1

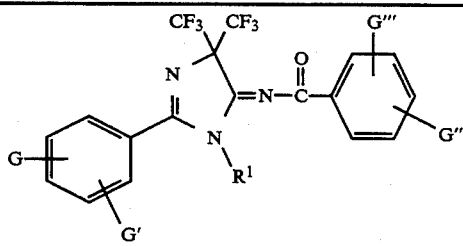

| Ex. # | R¹ | G | G'' | G' | G''' | mp (°C.) |
|---|---|---|---|---|---|---|
| 1 | CH₃ | H | H | H | H | 80–81 |
| 2 | CH₃ | p-F | p-F | H | H | 112–113 |
| 3 | CH₃ | p-Cl | p-Cl | H | H | 94–96 |
| 4 | CH₃ | m-CH₃ | m-CH₃ | H | H | 113–114 |
| 5 | CH₃ | p-CH₃ | p-CH₃ | H | H | Semi-Solid |
| 6 | H | H | H | H | H | 134–135 |
| 7 | H | p-Cl | p-Cl | H | H | 182–183 |
| 8 | H | m-CH₃ | m-CH₃ | H | H | 118–120 |
| 9 | H | p-CH₃ | p-CH₃ | H | H | 136–137 |
| 9a | CH₃ | p-F | O(CH₂)₃CH₃ | H | H | 106–107 |
| 9b | H | p-F | p-F | H | H | 161.9–163.9 |
| 9c | CH₂CH₃ | p-F | p-F | H | H | oil |
| 9d | CH₃ | p-CN | p-F | H | H | — |
| 9e | CH₃ | p-CF₃ | p-CF₃ | m-NO₂ | H | — |
| 9f | CH₃ | p-OCCH₃ (O=) | p-OCCH₃ (O=) | H | H | — |
| 9g | CH₃ | p-SCH₃ | p-SCH₃ | H | H | — |
| 9h | CH₃ | p-NO₂ | p-NO₂ | H | H | — |
| 9i | CH₃ | p-NO₂ | p-NO₂ | m-CF₃ | m-CF₃ | — |
| 9j | CH₃ | p-CN | p-CN | H | H | — |
| 9k | CH₃ | p-CH₃SO₂ | p-N₃ | m-F | H | — |
| 9l | H | m-CN | m-CN | H | H | — |
| 9m | CH₃ | p-N₃ | p-N₃ | H | H | — |
| 9n | CH₃ | p-CF₃SO₂ | p-OC₄H₉-n | H | m-CH₃ | — |
| 9o | CH₃ | p-CN | p-C₆H₁₃-n | H | H | — |
| 9p | CH₃ | p-N(O)(CH₃)₂ | p-(CH₃)₂CC₆H₄ | H | m-F | — |
| 9q | CH₃ | p-(CH₃)₂N | p-CO₂H | H | H | — |

Notes.

Example 1: MS m/e 414; ¹H NMR(CDCl₃) δ 3.10(s, 3H, NCH₃), 7.43–7.66(m, 8H, H$_{arom}$), 8.00–8.03(m, 2H, H$_{arom}$).

Example 2: MS m/e 449; ¹H NMR(CDCl₃) δ 3.13(s, 3H, NCH₃), 7.13–7.30(m, 4H, H$_{arom}$), 7.73(m, 2H, H$_{arom}$), 8.06(m, 2H, H$_{arom}$).

Example 3: MS m/e 481; ¹H NMR(CDCl₃) δ 3.10(s, 3H, NCH₃), 7.43–7.66(m, 6H, H$_{arom}$), 7.90–7.97(m, 2H, H$_{arom}$).

Example 4: MS m/e 442; ¹H NMR(CDCl₃) = 2.40(s, 6H, 2ArCH₃), 3.07(s, 3H, NCH₃), 7.33–7.50(m, 6H, H$_{arom}$), 7.77–7.83(m, 2H, H$_{arom}$).

Example 5: MS m/e 442; ¹H NMR(CDCl₃) δ 3.00(s, 6H, ArCH₃), 3.13(s, 3H, NCH₃), 7.27–7.37(m, 4H, H$_{arom}$), 7.57(d, 2H, J=7Hz, H$_{arom}$), 7.90(d, 2H, J = 7Hz, H$_{arom}$).

Example 6: MS m/e 400; ¹H NMR(CDCl₃) δ 7.47–7.70(m, 6H, H$_{arom}$), 8.00–8.03(m, 2H, H$_{arom}$), 8.33–8.37(m, 2H, H$_{arom}$), 11.73(s, 1H, NH).

Example 7: MS m/e 468; ¹H NMR(CDCl₃) δ 7.43–7.53(m, 4H, H$_{arom}$), 7.93–8.00(m, 2H, H$_{arom}$), 8.20–8.23(m, 2H, H$_{arom}$), 11.73(s, 1H, NH).

Example 8: MS m/e 428; ¹H NMR(CDCl₃) = 2.50(2s, 6H, 2ArCH₃), 7.43–7.57(m, 4H, H$_{arom}$), 7.77–7.90(m, 2H, H$_{arom}$), 8.17–8.23(m, 2H, H$_{arom}$), 11.70(s, 1H, NH).

Example 9: MS m/e 428; ¹H NMR(CDCl₃)δ 2.46(2s, 6H, 2ArCH₃), 7.27–7.40(m, 4H, H$_{arom}$), 7.87–7.90(m, 2H, H$_{arom}$), 8.23–8.30(m, 2H, H$_{arom}$), 11.70(s, 1H, NH).

EXAMPLE 9R

Preparation of N-[2,cyclohexyl-4,5-dihydro-4,4-bis(trifluoromethyl), 1H-imidazol-5-ylidene]-4-fluorobenzene carboxamide Part A To a solution of α,α-bis(trifluoromethyl)-4,5-bis(4-fluorophenyl)-1-methyl-1H-imidazole-2-methanamine (3.38 gr, 7.8 mmole) in pyridine (1.7 gr) was added cyclohexane carbonyl chloride (3.5 gr, 23.9 mmole). The reaction mixture was heated at 130° C. for 4 hours. The mixture was purified by column chromatography, eluting with hexane, then mixture of hexane-ethylacetate (9:1) to give 5-cyclohexyl-2,3-bis(4-fluorophenyl)-7,7-bis(trifluoromethyl)-7H-imidazo[1,5-A]-imidazole (1.88 gr, 37%) as a white solid: mp 162.2–162.6. Anal.

Calcd for C₂₅H₁₉F₈N₃:C,58.60;H,3.54;N,8.20. Found: C,58.43;H,3.79;N,8.16.

Part B

To a solution of 5-cyclohexyl-2,3-bis(4-fluorophenyl)-7,7-bis(trifluoromethyl)-7H-imidazo[1,5-A]imidazole (3.88 gr, 7.6 mmole) in chloroform (300 ml) was added m-chloroperbenzoic acid (MCPBA, 2.6 gr, 15.2 mmole). The mixture was refluxed under nitrogen for one hour. Then additional MCPBA (1.3 gr, 7.6 mmole) was added and the mixture was refluxed for one hour. The mixture was worked up and columned as described in Example 2 Method A to give the title compound (0.56 gr, 17%): mp 128–128.6 MS m/e 424 (M⁺ +H). Compounds listed in Table 1.1 were prepared according to the procedure of Example 9R.

TABLE 1.1

[Structure: imidazoline ring with CF₃, CF₃ substituents at 4-position, Ar¹ at 2-position, =N-R² and N-R¹ substituents]

| Ex. # | Ar¹ | R² | R¹ | mp (°C) |
|---|---|---|---|---|
| 9r | cyclohexyl | -C(O)-C₆H₄-F (para) | CH₃ | 127.6–129.9 |
| 9s | cyclohexyl | -C(O)-C₆H₄-F (para) | H | 128.0–128.6 |
| 9t | -C₆H₁₃ | -C(O)-C₆H₄-F (para) | H | ND |

EXAMPLE 10

Preparation of N-[4,4-bis-(trifluoromethyl)-2-(4-fluorophenyl)-4,5-dihydro-1-methyl-1H-imidazol-5-yl]-4-fluorobenzamide

Method A

To a solution of N-[4,4-bis(trifluoromethyl)-2-(4-fluorophenyl)-4,5-dihydro-1-methyl-1H-imidazol-5-ylidene]-4-fluorophenylbenzamide (8.8 g, 19.6 mmole) in anhydrous tetrahydrofuran (100 mL) at −78° C. under nitrogen was added dropwise lithium aluminum hydride in tetrahydrofuran (40 mL of 1M solution). The reaction mixture was stirred at room temperature for two hours, cooled at 0° C., quenched with water then extracted with methylene chloride. The organic layer was washed successively with saturated sodium bicarbonate solution, water and saturated sodium chloride solution, and dried over anhydrous magnesium sulfate. The solvent was removed under vacuum. The residue was triturated with hexane to give the title compound (5.65 g, 75%) as a white solid: mp 145°–146°; MS m/e 452 (M⁺+H); ¹H NMR (CDCl₃/TMS) δ 2.97 (s,3H,NHCH₃), 6.43(d,1H,J=7 Hz, CH), 6.63(d,1H,J=7 Hz,NH), 7.13–7.27(m,4H,H$_{arom}$), 7.60–7.70(m,2H,H$_{arom}$), 7.83–7.90(m,2H,H$_{arom}$). Anal. Calcd for C₁₉H₁₃N₃OF₈: C,50.57; H,2.90; N,9.31. Found: C,50.79; H,3.05; N,9.61.

Method B

To a solution of N-[4,4-bis(trifluoromethyl)2-(4-fluorophenyl-4,5-dihydro-1-methyl-1H-imidazol-5-ylidene]-4-fluorobenzamide (1.8 g, 4 mmole) in ethanol (50 mL) at room temperature under nitrogen, was added portionwise sodium borohydride (170 mg, 4.5 mmole). The reaction mixture was heated at reflux for three hours, and then stirred at room temperature overnight. The reaction mixture was cooled in an ice bath, quenched with water and hydrochloric acid (10 mL, 1N solution), made basic using sodium hydroxide (1N) and then extracted with ether. The organic layer was washed successively with sodium hydroxide (1N), water and saturated sodium chloride solution, dried over anhydrous magnesium sulfate. The solvent was removed under vacuum and the residue was purified by column chromatography, eluted with hexane followed by hexane-ethyl acetate (20:1 to 50:50) to give two products. The major product (0.8 g, 45%) is the same as the product of Example 10, Method A: mp 145°–146°; MS m/e 452(M⁺+H); ¹H NMR (CDCl₃/TMS) δ 2.97(s,3H,NCH₃), 6.43(d,1H, J=7 Hz, CH), 6.63(d,1H,J=7 Hz,NH), 7.13–7.27(m,4H,H$_{arom}$), 7.60–7.70(m,2H,H$_{arom}$), 7.83–7.90(m,2H,H$_{arom}$). The minor product, N-[2-(4-fluorophenyl)-2,3,4,5-tetrahydro-1-methyl-4,4-bis(trifluoromethyl)-1H-imidazol-5-ylidene]-4-fluorobenzamide, (0.5 g, 27%) was isolated as a solid: mp 132°–133°; MS m/e 452 (M⁺+H); ¹H NMR (CDCl₃/TMS) δ 2.57(s,3H,CH₃), 3.17(d,1H,J=7 Hz,NH), 5.63(d,1H,J=7 Hz,CH), 7.03–7.20(m,4H,H$_{arom}$), 7.40–7.50(m,2H,H$_{arom}$), 8.03–8.13(m,2H,H$_{arom}$).Anal. Calcd for C₁₉H₁₃N₃OF₈: C,50.57; H,2.90; N,9.31. Found: C,50.34; H,2.68; N,9.15.

EXAMPLE 10A

Preparation of N-[4,4-bis(trifluoromethyl)2-(4-fluorophenyl)-4,5-dihydro-1-methyl-1H-imidazol-5-yl]-4-fluorophenyl-N-methylbenzamide Sodium hydride (1.5 g, 3.75 mmole) 60% suspension in oil was washed with hexane and then it was suspended in anhydrous dimethylformamide (50 mL). To this suspension was added portionwise N-[4,4-bis(trifluoromethyl)-2-(4-fluorophenyl)-4,5-dihydro-1-methyl-1H-imidazol-5-yl]-4-fluorobenzamide (6.85 g, 15 mmole) and the mixture was allowed to stir at room temperature for one hour. Iodomethane (4.50 g, 30 mmole) was added dropwise and the reaction mixture was allowed to stir at room temperature overnight. The reaction mixture was poured into water and extracted with ether. The organic layer was washed successively with water and saturated sodium chloride solution, dried over anhydrous magnesium sulfate and concentrated to give the title compound (6.46 g, 91%) as a crystalline solid: mp 112°–113°; MS m/e 466(M⁺+M); ¹H NMR (CDCl₃/TMS) δ 2.93(s,3H,NCH₃), 3.00(s,3H,NCH₃), 6.79(s,1H,CH), 7.17(m,4H,H$_{arom}$), 7.43–7.50(m,2H,H$_{arom}$), 7.63–7.70(m,2H,H$_{arom}$).

EXAMPLE 11

Preparation of N-[4,4-bis(trifluoromethyl)-2-(4-fluorophenyl)-4,5-dihydro-1-methyl-1H-imidazol-5-yl]-4-butoxy-N-methylbenzamide

Part A

To a solution of N-[4,4-bis(trifluoromethyl)-2-(4-fluorophenyl)-4,5-dihydro-1-methyl-1H-imidazol-5yl]-4-fluoro-N-methylbenzamide (6.46 g, 13.9 mmole) in ether (300 mL) was added potassium tert-butoxide (9.35 g, 6 equiv.) and water (0.5 g, 2 equiv.). The reaction mixture was allowed to stir overnight at room temperature. The suspension was poured into water and the phases were separated. The organic layer was washed successively with water, then saturated sodium chloride solution, dried over anhydrous magnesium sulfate and concentrated under vacuum to give a yellow oil (4.83 g, 100%). Treatment with hydrochloric acid (1M) in ether gave the 4,4-bis(trifluoromethyl)-1)-2-(4-fluorophenyl)-4,5-dihydro-5-amine-N,N-1,5-dimethyl-1H-imidazole hydrochloride as a white solid: mp 206°–207°; MS m/e 344 (M⁺+H); ¹H NMR (CDCl₃/TMS) δ

2.67(s,3H,NCH₃), 2.93(s,3H,NCH₃), 4.67(s,1H,CH), 7.10–7.20(m,2H,H$_{arom}$), 7.53–7.63(m,2H,H$_{arom}$); Anal. Calcd for C$_{13}$H$_{12}$N$_3$F$_7$·HCl: C,41.12; H,3.45; N,11.07; Found: C,41.36; H,3.79; N,11.24.

Part B

To a solution of 4,4-bis(trifluoromethyl)-2-(4-fluorophenyl)-4,5-dihydro-5-amine-N,N-1,5-dimethyl-1H-imidazole (0.34 g, 1 mmole) in a dichloromethane (10 mL) was added p-butoxybenzoyl chloride (0.64 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (20:1 to 50:50). The crude product (0.48 g, 92%) was recrystallized from dichloromethane-methanol-petroleum ether to give the title compound as a white solid: mp 84°–85°; MS m/e 520 (M⁺+H); ¹H NMR (CDCl₃/TMS) δ 1.00(t,3H,J=7 Hz,CH₃), 1.43–1.60(m,2H,CH₂), 1.73–1.87(m,2H,CH₂), 2.97(s,3H,NCH₃), 3.00(s,3H,NCH₃), 4.00; (t,2H,J=7 Hz,OCH₂), 6.73(s,1H,CH), 6.93, (d,2H,J=10Hz, H$_{arom}$), 7.13–7.27(m,2H,H$_{arom}$), 7.43(d,2H,J=7 Hz,H$_{arom}$), 7.63–7.70(m,2H,H$_{arom}$). Anal. Calcd for C$_{24}$H$_{24}$N$_3$O$_2$F$_7$: C,55.49; H,4.66; N,8.09. Found: C,55.27; H,4.56; N,8.02.

EXAMPLE 12

Preparation of N-[4,4-bis(trifluoromethyl)-2-(4-fluorophenyl)-4,5-dihydro-1-methyl-1H-imidazol-5-yl]-4-methoxy-N-methylbenzamide To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (10 mL) was added p-anisoyl chloride (0.51 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1 N) and saturated sodium chloride solution, dried over anhydrous magnesium sulfate and concentrated under vacuum. The residue was purified by flash chromatography eluting with hexane and hexane-ethyl acetate (20:1 to 50:50). The crude product was recrystallized from dichloromethane-methanol-petroleum ether to give the title compound (0.25 g, 52%) as a white solid: mp 136°–137°; MS m/e 478 (M⁺+H). ¹H NMR (CDCl₃/TMS) δ 2.93(s,3H,NCH₃), 2.97(s,3H,NCH₃), 3.83(s,3H,OCH₃), 6.73(s,1H,CH), 6.97(d,2H,J=7 Hz,H$_{arom}$), 7.13–7.20(m,2H,H$_{arom}$), 7.43(d,2H,J=7 Hz,H$_{arom}$); 7.60–7.70(m,2H,H$_{arom}$).

EXAMPLE 13

Preparation of N-[4,4-bis(trifluoromethyl)-2-(4-fluorophenyl)-4,5-dihydro-1-methyl-1H-imidazol-5-yl]-4-(1,1-dimethylethyl)-N-methylbenzamide To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (10 mL) was added p-(t-butyl)benzoyl chloride (0.59 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (20:1 to 50:50). The crude product (0.40 g, 79%) was recrystallized from dichloromethane-methanol-petroleum ether to give the title compound (80 mg, 16%) as a white solid: mp 129°–130°; MS m/e 504 (M⁺+H); ¹H NMR (CDCl₃/TMS) δ 1.33(s,9H,(CH₃)₃), 2.93(s,3H,NCH₃), 3.00(s,3H,NCH₃), 6.83(s,1H,CH), 7.17–7.27(m,2H,H$_{arom}$), 7.20–7.50(m,4H,H$_{arom}$), 7.63–7.70(m,2H,H$_{arom}$). Anal. Calcd for C$_{24}$H$_{24}$N$_3$OF$_7$: C,57.26; H,4.81; N,8.35. Found: C,57.20; H,4.82; N,8.29.

EXAMPLE 14

Preparation of N-[4,4-bis(trifluoromethyl)-2-(4-fluorophenyl)-4,5-dihydro-1-methyl-1H-imidazol-5-yl]-N-methyl-4-nitrobenzamide To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (10 mL) was added p-nitrobenzoyl chloride (0.56 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (20:1 to 50:50). The crude product (0.40 g, 81%) was recrystallized from dichloromethane-methanol-petroleum ether to give the title compound (200 mg, 41%) as a white solid: mp 174°–175°; MS m/e 493 (M⁺+H); ¹H NMR (CDCl₃/TMS) δ 2.90(s,3H,NCH₃), 3.07(s,3H,NCH₃), 6.77(s,1H,CH), 7.17–7.27(m,2H,H$_{arom}$), 7.60–7.73(m,4H,H$_{arom}$), 8.37(d,2H,J=7 Hz,H$_{arom}$). Anal. Calcd for C$_{20}$H$_{15}$N$_4$O$_3$F$_7$: C,48.79; H,3.07; N,11.38. Found: C,48.76; H,2.81; N,11.27.

EXAMPLE 15

Preparation of N-[4,4-bis(trifluoromethyl)-2-(4-fluorophenyl)-4,5-dihydro-1-methyl-1H-imidazol-5-yl]-N-methyl-[1,1'-biphenyl]-4-carboxamide To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (10 mL) was added p-biphenyl carbonyl chloride (0.65 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (20:1 to 50:50). The crude product was recrystallized from dichloromethane-methanol-petroleum ether to give the title compound (0.09 g, 17%) as a white solid: MP 186°–187°; MS m/e 524 (M++H); $^1$H NMR (CDCl$_3$/TMS) δ 3.00(s,3H,NCH$_3$), 3.03(s,3H,NCH$_3$),6.87(s,1H,CH), 7.17–7.77(m,14H,H$_{arom}$). Anal. Calcd for C$_{26}$H$_{20}$N$_3$F$_7$O: C, 59.66; H,3.65; N,8.03. Found: C,59.48; H,3.72; N,7.89.

EXAMPLE 16

Preparation of
N-[4,4-bis(trifluoromethyl)-2-(4-fluorophenyl)-4,5-dihydro-1-methyl-1H-imidazol-5-yl]-N-methylheptanamide hydrochloride To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (10 mL) was added heptanoyl chloride (0.45 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (20:1 to 50:50). The crude product (0.20 g, 41%) was treated with HCl in ether and recrystallized from dichloromethane-methanol-petroleum ether to give the title compound as a white solid: mp 134°–136°; MS m/e 456 (M++H); $^1$H NMR (CDCl$_3$/TMS) δ 1.90(m,3H,CH$_3$), 1.33(m,6H,(CH$_2$)$_3$), 1.70(m,2H,CH$_2$), 2.47(m,2H,CH$_2$), 3.00(s,3H,NCH$_3$), 3.23(s,3H,NCH$_3$), 7.03(s,1H,CH), 7.20–7.40(m,2H,H$_{arom}$), 7.93–8.17(m,2H,H$_{arom}$).

EXAMPLE 18

Preparation of
N-[4,4-bis(trifluoromethyl)-2-(4-fluorophenyl)-4,5-dihydro-1-methyl-1H-imidazol-5-yl]-N,5-dimethyl-hexanamide hydrochloride To a solution of 5-methylhexanoic acid (0.53 g, 4 mmole) in dichloromethane was added oxalyl chloride (0.77 g, 6 mmole). The reaction mixture was stirred at room temperature for 2 hours and then evaporated under vacuum to give crude 5-methylhexanoyl chloride. To a solution of 4,4-bis(trifluoromethyl)-2-(4-fluorophenyl)-4,5-dihydro-5-amine-N,N-1,5-dimethyl-1H-imidazole (0.60 g, 1.76 mmole) in dichloromethane (15 mL) was added 5-methylhexanoyl chloride and pyridine (0.42 g, 5 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (20:1 to 50:50). The crude product (0.42 g, 85%) was treated with HCl in ether and recrystallized from dichloromethane-methanol-petroleum ether to give the title compound as a white solid: mp 112°–114°; MS m/e 456 (M++H); $^1$H NMR (CDCl$_3$/TMS) δ 0.90(s,3H,CH$_3$), 0.93(s,3H,CH$_3$), 1.27(m,2H,CH$_2$), 1.67(m,3H,CH$_2$CH), 2.47(m,2H,CH$_2$), 3.00(s,3H,NCH$_3$), 3.23(s,3H,NCH$_3$), 7.03(s,1H,CH), 7.33(m,2H,H$_{arom}$), 8.00(m,2H,H$_{arom}$).

EXAMPLES 25 AND 26

Preparation of the diastereomers of
N-[4,4-bis(trifluoromethyl)-2-(4-fluorophenyl)-4,5-dihydro-1-methyl-1H-imidazol-5-yl]-camphanylamide To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (10 ml) was added camphanyl chloride (0.85 g, 3 mmole) and pyridine (0.24 g, 3 mmole). The reaction mixture was stirred overnight at room temperature under nitrogen. The crude reaction mixture was quenched with water and extracted with ether. The organic layer was washed successively with water, sodium hydroxide (1N) and saturated sodium chloride solution, dried over anhydrous magnesium sulfate and concentrated under vacuum. The residue was purified by flash chromatography eluting with hexane and hexane-ethyl acetate (10:1) to give the diastereomers which were recrystallized from hexane-dichloromethane mixture. The diastereomer that eluted first (100 mg, 19%) is a solid: mp 126°–127°; $[α]^{25}_D = -8.91°$ (c,0.606, MeOH); MS m/e 524(M++H); $^1$H NMR (CDCl$_3$/TMS) δ 1.03(s,3H,CH$_3$), 1.13(s,3H,CH$_3$), 1.23(s,3H,CH$_3$), 1.63–2.43(m,4H,(CH$_2$)$_2$), 2.97(s,3H,NCH$_3$), 3.13(s,3H,NCH$_3$), 6.53(s,1H,C)H, 7.20(m,2H,H$_{arom}$), 7.67(m,2H,H$_{arom}$). Anal. Calcd for C$_{23}$H$_{24}$N$_3$F$_7$O$_3$: C,52.78; H,4.62; N,8.03. Found: C,52.70; H,4.65; N,7.97. The diastereomer that eluted last (80 mg, 15%) is a solid: mp 87–88; $[α]^{25}_D = +7.04°$ (c,0.610, MeOH): MS m/e 524(M++H); $^1$H NMR (CDCl$_3$/TMS) δ 1.03(s,3H,CH$_3$), 1.13(s,3H,CH$_3$), 1.17(s,3H,CH$_3$), 1.60–2.67(m,4H,(CH$_2$)$_2$), 2.97(s,3H,NCH$_3$), 3.17(s,3H,NCH$_3$(, 6.60(s,1H,CH), 7.20(m,2H,H$_{arom}$), 7.67(m,2H,H$_{arom}$). Anal. Calcd for C$_{23}$H$_{24}$N$_3$F$_7$O$_3$: C,52.78; H,4.62; N,8.03. Found: C,52.82; H,4.39; N,8.03.

EXAMPLE 27

Preparation of
N-[4,4-bis(trifluoromethyl)-2-(4-fluorophenyl)-4,5-dihydro-1-methyl-1H-imidazol-5-yl]-N'-4-isopropylphenyl-N-methylurea To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (2 mL) and hexane (10 mL) was added 4-isopropylphenyl isocyanate (0.45 g, 3 mmole). The reaction mixture was stirred overnight at room temperature under nitrogen. The crude reaction mixture was quenched with water and extracted with ether. The organic layer was washed succesively with water, sodium hydroxide (1N), and saturated sodium chloride solution, dried over anhydrous magnesium sulfate and concentrated under vacuum. The residue was purified by flash chromatography eluting with hexane and hexane-ethyl acetate (10:1) to give the title compound (0.20 g, 40%) as a white solid: mp 203°–204°; MS m/e 505 (M++H); $^1$H NMR (CDCl$_3$/TMS) δ 1.23(s,3H,CH$_3$), 1.27(s,3H,CH$_3$), 2.93(m,1H,CH), 3.00(s,6H,2 NCH$_3$), 6.53(s,1H,NH), 6.67(s,1H,CH), 7.20–7.43(m,6H,H$_{arom}$), 7.67–7.77(m,2H,H$_{arom}$). Anal. Calcd for C$_{23}$H$_{23}$N$_4$F$_7$O: C,54.76; H,4.60; N,11.11. Found: C,54.85; H,4.62; N,11.02.

EXAMPLE 28

Preparation of
N-[4,4-bis(trifluoromethyl)-2-(4-fluorophenyl)-4,5-dihydro-1-methyl-1H-imidazol-5-yl]-N'-2,4-difluorophenyl-N-methylurea To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (2 mL) and hexane (10 mL) was added 2,4-difluorophenyl isocyanate (0.47 g, 3 mmole). The reaction mixture was stirred overnight at room temperature under nitrogen. The crude reaction mixture was quenched with water and extracted with ether. The organic layer was washed successively with water, sodium hydroxide (1N), and saturated sodium chloride solution, dried over anhydrous magnesium sulfate and concentrated under vacuum. The residue (0.51 g, 100%) was purified by flash chromatography eluting with hexane and hexane-ethyl acetate (10:1) to give the title compound (100 mg, 20%) as a white solid: mp 176°-177°; MS m/e 499 (M++H); $^1$H NMR (CDCl$_3$/TMS) δ 2.97(s,6H,2 NCH$_3$), 6.57(s,1H,NH), 6.67(s,1H,CH), 6.85–6.93(m,2H,H$_{arom}$), 7.17–7.27(m,2H,H$_{arom}$), 7.63–7.73(m,2H,H$_{arom}$), 8.00–8.13(m,1H,H$_{arom}$). Anal. Calcd for C$_{20}$H$_{15}$F$_9$N$_4$O: C,48.20; H,3.03; N,11.24. Found: C,48.13; H,2.97; N,11.08

EXAMPLE 29

Preparation of
N-[4,4-bis(trifluoromethyl)-2-(4-fluorophenyl)-4,5-dihydro-1-methyl-1H-imidazol-5-yl]-N'-octyl-N-methylurea hydrochloride To a solution of 4,4-bis(trifluoromethyl)-2-(4-fluorophenyl)-4,5-dihydro-5-amine-N,N-1,5-dimethyl-1H-imidazole (0.34 g, 1 mmole) in dichloromethane (2 mL) and hexane (10 mL) was added n-octyl isocyanate (0.47 g, 3 mmole). The reaction mixture was stirred over 3 days at room temperature then refluxed for 4 hours under nitrogen. The crude reaction mixture was quenched with water and extracted with ether. The organic layer was washed successively with water, sodium hydroxide (1N), and saturated sodium chloride solution, dried over anhydrous magnesium sulfate and concentrated under vacuum. The residue was treated with HCl in ether then purified by flash chromatography eluting with hexane and hexane-ethyl acetate (10:1) to give the title compound (50 mg, 9%) as a light brown solid: mp 45°-47°; MS m/e 499 (M++H); $^1$H NMR (CDCl$_3$/TMS) δ 0.90(m,3H,CH$_3$), 1.27(m,12H,(CH$_2$)$_6$), 2.60(d,3H,NCH$_3$), 2.93(s,3H,NCH$_3$), 3.13(m,2H,CH$_2$), 4.77(m,1H,NH), 6.60(s,1H,CH), 7.17(m,2H,H$_{arom}$), 7.63(m,2H,H$_{arom}$).

EXAMPLE 30

Preparation of
N-[4,4-bis(trifluoromethyl)-2-(4-fluorophenyl)-4,5-dihydro-1-methyl-1H-imidazol-5-yl]-4-ethoxybenzamide To a solution of N-[4,4-bis(trifluoromethyl)-2-(4-fluorophenyl)-4,5-dihydro-1H-imidazol-5-yl]-4-fluorobenzamide (0.26 g, 0.6 mmole) in ethanol (10 mL) was added sodium hydroxide solution (1 mL, 50%). The reaction mixture was allowed to reflux overnight. The solution was cooled to room temperature, poured into water and extracted with ether. The organic layer was washed successively with water, and saturated sodium chloride solution, dried over anhydrous magnesium sulfate and concentrated under vacuum. The residue was purified by HPLC with 85:15 hexane-ethyl acetate to give the title compound (20 mg, 7%) as a white solid: mp 115°-116°; $^1$H NMR (CDCl$_3$/TMS) δ 1.43(t,J=7 Hz,3H,CH$_3$), 2.97(s,3H,NCH$_3$), 4.07(q,J=7 Hz,2H,CH$_2$), 6.37(d,1H,J=14 Hz,CH), 6.60(d,2H,J=14 Hz,NH), 6.97(d,2H),J=10 Hz,H$_{arom}$), 7.17(q,2H,J=7 Hz,H$_{arom}$), 7.57(d,2H,J=10 Hz,H$_{arom}$), 7.83(m,2H,H$_{arom}$).

EXAMPLES 31 AND 32

Preparation of
N-[4,4-bis(trifluoromethyl)-2-(4-fluorophenyl)-4,5-dihydro-1-methyl-1H-imidazol-5-yl]-4-(1-piperidinyl)benzamide (Example 31) and
N-[4,4-bis(trifluoromethyl)-4,5-dihydro-1-methyl-2-[4-(1-piperidinyl)phenyl]-1H-imidazol-5-yl]-4-fluorobenzamide (Example 32)

To a solution of N-[4,4-bis(trifluoromethyl)-2-(4-fluorophenyl)-4,5-dihydro-1H-imidazol-5-yl]-4-fluorobenzamide (0.9 g, 2 mmole) in dimethyl sulfoxide (5 mL) was added potassium carbonate (0.83 g, 3 equiv.) and piperidine (0.51 g, 3 equiv.). The reaction mixture was heated at 145° overnight under nitrogen. The solution was cooled to room temperature, poured into water and extracted with dichloromethane. The organic layer was washed with water and saturated sodium chloride, dried over anhydrous magnesium sulfate, and concentrated under vacuum. The residue was purified by MPLC with 9:1 hexane-ethyl acetate to give two products. N-[4,4-bis(trifluoromethyl)-2-(4-fluorophenyl)-4,5-dihydro-1-methyl-1H-imidazol-5-yl]-4-(1-piperidinyl)benzamide (160 mg, 15%) was isolated as a white solid: mp 128°-129° ; MS m/e 517 (M++H); $^1$H NMR (CDCl$_3$/TMS) δ 1.67(m,6H,(CH$_2$)$_3$), 2.93(s,3H,NCH$_2$), 3.33(m,4H,CH$_2$NCH$_2$), 6.43–6.60(m,2H,NH,CH), 6.90)d,2H,J=7, H$_{arom}$), 7.13–7.20(m,2H,H$_{arom}$), 7.60–7.73(m,2H,H$_{arom}$). N-[4,4-bis(trifluoromethyl)-4,5-dihydro-1-methyl-2-[4-(1-piperidinyl)phenyl]-1H-imidazol-5-yl]-4-fluorobenzamide (80 mg, 8%) was isolated as a white solid: mp 123°-124°; MS m/e 517 (M++H); $^1$H NMR (CDCl$_3$/TMS ( δ 1.67(m,6H,(CH$_2$)$_3$), 3.00(s,3H,NCH$_3$), 3.30(m,4H,CH$_2$NCH$_2$), 6.37(d,1H,CH), 6.60(m,2H,NH), 6.90(d,2H,J=7,H$_{arom}$), 7.13–7.22(m,2H,H$_{arom}$), 7.53(d,2H,J=7,H$_{arom}$), 7.80–7.90(m,2H,H$_{arom}$).

EXAMPLE 33

Preparation of
N-[4,4-bis(trifluoromethyl)-4,5-dihydro-1-methyl-2-[4-(1-piperidinyl)phenyl]-1H-imidazol-5-yl]-N-methylheptanamide, hydrochloride To a solution of N-[4,4-bis(trifluoromethyl)-2-(4-fluorophenyl)-4,5-dihydro-1H-imidazol-5-yl]-N-methylheptanamide hydrochloride (0.20 g, 0.4 mmole) in dimethyl sulfoxide (5 mL) was added potassium carbonate (0.29 g, 1.2 mmole) and piperidine (0.10 g, 1.2 mmole). The reaction mixture was heated at 145° overnight under nitrogen. The solution was cooled to room temperature, poured into water and extracted with ether. The ether layer was washed with 1N HCL to give unreacted starting material. The aqueous layer was made basic and it was extracted with ether. The organic layer was washed with water and saturated sodium chloride, dried over anhydrous magnesium sulfate, and concentrated under vacuum. The residue was treated with HCl in ether to give the title compound (50 mg, 22%) as a semi solid: MS m/e 521 (M++H); $^1$H NMR (CDCl$_3$/TMS) δ 0.90(m,3H,CH$_3$), 1.30(m,8H,(CH$_2$)$_4$), 1.67(m,6H,(CH$_2$)$_3$), 2.40(t,2H,CH$_2$), 2.90(s,3H,NCH$_3$), 2.97(s,3H,NCH$_3$), 3.30(m,4H,2CH$_2$), 6.53(s,1H,CH), 6.90(d,2H,H$_{arom}$), 7.53(d,2H,H$_{arom}$).

EXAMPLE 34

Preparation of
N-[4,4-bis(trifluoromethyl)-2-(4-methoxyphenyl)-4,5-dihydro-1-methyl-1H-imidazol-5-yl]-N,5-dimethylhexanamide hydrochloride To N-[4,4-bis(trifluoromethyl)-2-(4-fluorophenyl)-4,5-dihydro-1H-imidazol-5-yl]-N,5-dimethylhexanamide (0.05 g, 0.1 mmole) was added sodium methoxide solution (10 mL, 25%). The reaction mixture was allowed to reflux for 3 hours. The solution was cooled to room temperature, poured into water and extracted with ether. The organic layer was washed successively with water, and saturated sodium chloride solution, dried over anhydrous magnesium sulfate and concentrated under vacuum. The residue was treated with HCl in ether to give the title compound (50 mg, 99%) as a white solid: mp 68°-69°; MS m/e 468 (M++H); $^1$H NMR (CDCl$_3$/TMS) δ 0.87(s,3H,CH$_3$), 0.90(s,3H,CH$_3$), 1.27(m,2H,CH$_2$), 1.60(m,3H,CH$_2$CH); 2.37(m,2H,CH$_2$), 2.90(m,6H,2NCH$_3$), 3.83(s,3H,OCH$_3$), 6.60(s,1H,CH), 6.97(d,2H,H$_{arom}$), 7.60(d,2H,H$_{arom}$).

EXAMPLE Q AND R

Preparation of
N-[4,4-bis(trifluoromethyl)-2-(4-cyanophenyl)-4,5-dihydro-1-methyl-1H-imidazol-5-yl]-N-methyl-4-fluorobenzamide (Example Q) and
N-[4,4-bis(trifluoromethyl)-4,5-dihydro-1-methyl-2-[4-cyanophenyl]-1H-imidazol-5-yl]-N-methyl-4-cyanobenzamide (Example R)

To a solution of N-[4,4-bis(trifluoromethyl)-2-(4-fluorophenyl)-4,5-dihydro-1H-imidazol-5-yl]-4-fluoromethylbenzamide (0.46 g, 1 mmole) in dimethyl sulfoxide (5 mL) was added potassium carbonate (0.41 g, 3 equiv.) and potassium cyanide (0.47 g, 3 equiv.). The reaction mixture was heated at 120° overnight under nitrogen. The solution was cooled to room temperature, poured into water and extracted with dichloromethane. The organic layer was washed with water and saturated sodium chloride, dried over anhydrous magnesium sulfate, and concentrated under vacuum. The residue was purified on silica gel eluting with hexane, then a mixture of hexane-ethylacetate (20:1 to 50:50) to give two products. N-[4,4-bis(trifluoromethyl)-2-(4-cyanophenyl)-4,5-dihydro-1-methyl-1H-imidazol-5-yl]-4-fluoromethylbenzamide (130 mg, 28%) was isolated as a white solid: mp 189°-190°; MS m/e 473 (M++H); $^1$H NMR (CDCl$_3$/TMS) δ 2.93 (s,3H,NCH$_3$), 2.98(s,3H,NCH$_3$), 6.80(bs,1H,CH), 7.18(m,2H,H$_{arom}$), 7.45(m,2H,H$_{arom}$), 7.80(m,4H,H$_{arom}$). Anal. Calcd for C$_{21}$H$_{15}$N$_4$OF$_7$: C,53.40; H,3.20; N,11.86. Found: C,53.12; H,3.16; N,11.69. N-[4,4-bis(trifluoromethyl)-4,5-dihydro-1-methyl-2-[4-cyanophenyl)-1H-imidazol-5-yl]-4-cyanomethylbenzamide (40 mg, 8%) was isolated as a white solid: mp 128°-129°; MS m/e 480 (M++H); $^1$H NMR (CDCl$_3$/TMS) δ 2.90(s,3H,NCH$_3$), 3.00(m,3H,NCH$_3$), 6.80(bs,1H,CH), 7.55(m,2H,H$_{arom}$), 7.80(m,6H,H$_{arom}$).

Recrystallization of N-[4,4-bis[trifluoromethyl)-4,5-dihydro-1-methyl-2-[4-cyanophenyl]-1H-imidazol-5-yl]-N-methyl-4-cyanobenzamide from methylene chloride-hexane gave the polymorphic crystalline form that melts at 132° to 134° C. Recrystallization from ethyl acetate-hexane gave a polymorphic form melting at 181°-183° C. X-ray powder diffraction showed that each polymorph has a distinct crystalline form. The polymorphs are interconvertible based on the solvent used for recrystallization. Differential scanning calorimetry of the compound of Example R resulted in three peaks at 131.7° C., 182.6° C., and 253.5° C., which correspond to polymorphic transitions from the 131° C. form to the 182.6° C. form, followed by decomposition at 253.5° C. The 132°-134° melting polymorph is 3 fold more water soluble that the 181°-183° C. melting polymorph and has greater oral bioavailability leading to improved systemic ACAT inhibitory activity, compared to the higher melting form.

Separation of [R] and [S] enautiomers of [4,4 bis(trifluoromethyl)-4,5-dihydro-1-methyl-2-[4-cyanophenyl]-1H-imidazole-5-yl]-N-methyl-4-cyano-benzamide(example 73, 74) and their sulfate salts (Ex. 75, 76).

The racemic mixture of the title compound was separated to the R and S enantiomers using HPLC with a Chiracel-OJ column eluted with 50% ethanol-hexane. Upon concentration, the enantiomers are triturated with hexane to give amorphous solid. The sulfate salt can be obtained by dissolving the amorphous solid in ether and adding sulfuric acid (conc) to give white solid which can be recrystalized from methanol-ether to give the sulfate salt of the [S] enautiomer:mp 181.-183.7 Anal. Calcd for C$_{22}$H$_{15}$F$_6$N$_5$O.H$_2$SO$_4$: C,45.76; H,2.97; N,12.13: S5.55. Found: C,46.22, H,3.13; 11.60; S,5.91.

The sulfate salt of the [R] enantiomer: mp 181.1-181.8 Analc. Calcd for C$_{22}$H$_{15}$F$_6$N$_5$O.H$_2$SO$_4$: C,45.76; H,2.97; N,12.13; S5.55. Found C,46.32; H,3.13; N,11.63; S,5.99.

The compounds of Examples 10-18, 22-23, 25-34, Q, R, and S and other compounds of Formula (I) wherein a is a single bond which have been prepared or could be prepared using the same or similar synthetic methods, are listed in Table 2 and Table 2.1.

TABLE 2

[Structure: substituted benzene ring with G and G' substituents, connected to C=N-C(CF₃)(CF₃)-CH(NR⁶R²)- with N-R¹ group]

| Ex. # | G | G' | R¹ | R⁶ | R² | mp (°C.) |
|---|---|---|---|---|---|---|
| 10 | p-F | H | CH₃ | H | —C(=O)—C₆H₄—4-F | 145–146 |
| 10A | p-F | H | CH₃ | H | —C(=O)—C₆H₄—4-F | 112–113 |
| 11 | p-F | H | CH₃ | H | —C(=O)—C₆H₄—4-O(CH₂)₃CH₃ | 84–85 |
| 12 | p-F | H | CH₃ | H | —C(=O)—C₆H₄—4-OCH₃ | 136–137 |
| 13 | p-F | H | CH₃ | H | —C(=O)—C₆H₄—4-C(CH₃)₃ | 129–130 |
| 14 | p-F | H | CH₃ | H | —C(=O)—C₆H₄—4-NO₂ | 174–175 |
| 15 | p-F | H | CH₃ | H | —C(=O)—C₆H₄—4-C₆H₅ | 186–187 |
| 16 | p-F | H | CH₃ | H | COC₆H₁₃ | 134–136 (HCl salt) |
| 17 | p-F | H | CH₃ | H | CO(CH₂)₁₀CH₃ | 72–74 (HCl salt) |
| 18 | p-F | H | CH₃ | H | CO(CH₂)₃CH(CH₃)₂ | 112–114 (HCl salt) |
| 22 | p-F | H | CH₃ | CH₃ | —C(=O)-2-thienyl | 111–112 |
| 23 | p-F | H | CH₃ | CH₃ | —C(=O)-2-furyl | 128–129 |
| 25 | p-F | H | CH₃ | CH₃ | —C(=O)-(camphanoyl: 1,7,7-trimethyl-2-oxabicyclo derivative) | 126–127 |

TABLE 2-continued
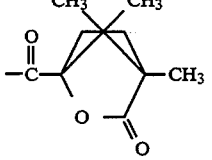
| Ex. # | G | G' | R¹ | R⁶ | R² | mp (°C.) |
|---|---|---|---|---|---|---|
| 26 | p-F | H | CH₃ | CH₃ |  | 87–88 |
| 27 | p-F | H | CH₃ | CH₃ | 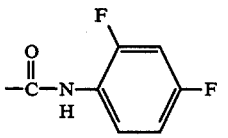 | 203–204 |
| 28 | p-F | H | CH₃ | CH₃ | 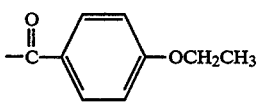 | 176–177 |
| 29 | p-F | H | CH₃ | CH₃ | CONHC₈H₁₇ | 45–47 (HCl salt) |
| 30 | p-F | H | CH₃ | H | 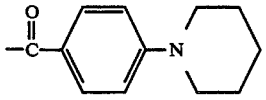 | 115–116 |
| 31 | p-F | H | CH₃ | H | 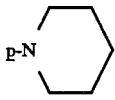 | 128–129 |
| 32 | 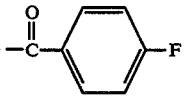 p-N | H | CH₃ | H | 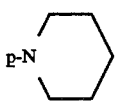 | 123–124 |
| 33 | 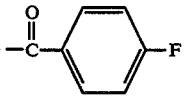 p-N | H | CH₃ | CH₃ | COC₆H₁₃ | Semi-Solid (HCl salt) |
| 34 | p-OCH₃ | H | CH₃ | CH₃ | CO(CH₂)₃CH(CH₃)₂ | 68–69 (HCl salt) |
| Q | p-CN | H | CH₃ | CH₃ | 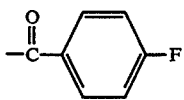 | 189–190 |
| R | p-CN | H | CH₃ | CH₃ | 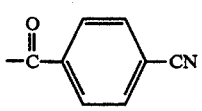 | 128–129 |

TABLE 2-continued
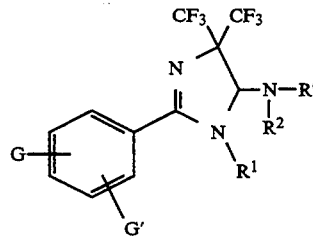
| Ex. # | G | G' | R¹ | R⁶ | R² | mp (°C.) |
|---|---|---|---|---|---|---|
| S | p-F | H | CH₃ | CH₃ | 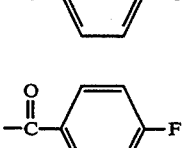 | 149.3–150.2 |
| 35 | p-CN | m-NO₂ | CH₃ | CH₃ | 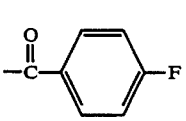 | |
| 36 | p-CF₃ | H | CH₃ | CH₃ | 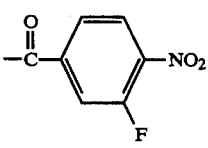 | |
| 37 | p-F | H | CH₃ | CH₃ | 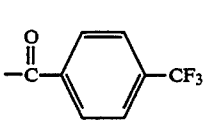 | |
| 38 | p-CN | H | CH₃ | CH₃ | COC₆H₁₃ | |
| 39 | p-NO₂ | m-Cl | CH₃ | CH₃ | COC₆H₁₃ | |
| 40 | p-F | H | CH₃ | CH₃ | 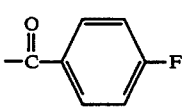 | |
| 41 | p-CO₂Et | H | CH₃ | CH₃ | 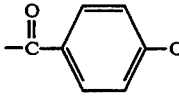 | |
| 42 | p-CN | H | CH₃ | CH₃ | 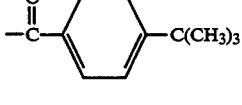 | 183.3–184.8 |
| 43 | p-CN | H | CH₃ | CH₃ | 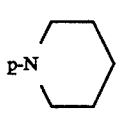 | |
| 44 | 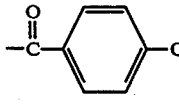 | m-CH₃ | CH₃ | CH₃ | 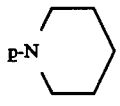 | |
| 45 | p-N (piperidine) | H | CH₃ | CH₃ | 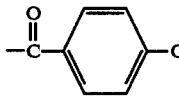 | 141.2–143.4 |

TABLE 2-continued

[Structure: 4,5-dihydroimidazole with 4,4-bis(CF₃), substituted phenyl (with G and G') at C-2, N1-R¹, and C5-N(R²)(R⁶)]

| Ex. # | G | G' | R¹ | R⁶ | R² | mp (°C.) |
|---|---|---|---|---|---|---|
| 46 | p-N(piperidinyl) | H | CH₃ | CH₃ | −C(O)−(4-biphenyl) | 189.5–191.5 |
| 47 | p-N(piperidinyl) | Cl | CH₃ | CH₃ | −C(O)−C₆H₄−4-F | |
| 48 | p-N(morpholinyl) | H | CH₃ | CH₃ | −C(O)−C₆H₄−4-F | 146–147 |
| 49 | p-OH | H | CH₃ | CH₃ | −C(O)−C₆H₁₃ | 198 |
| 50 | p-OCH₃ | H | CH₃ | CH₃ | −C(O)−C₆H₁₃ | semi-solid |
| 51 | p-F | H | CH₃ | CH₃ | −(CH₂)₆CH₃ | 152.4(d) |
| 52 | p-F | H | CH₃ | CH₃ | −C(O)−C₆H₄−4-N(CH₃)₂ | 128–129 |
| 53 | p-NO₂ | m-CF₃ | CH₃ | CH₃ | −C(O)−C₆H₄−4-OC₄H₉-n | |
| 54 | p-Cl | m-Cl | CH₃ | CH₃ | −C(O)−C₆H₄−4-C(CH₃)₃ | |
| 55 | p-N(piperidinyl) | H | CH₃ | CH₃ | −C(O)−C₆H₃−4-CN−3-NO₂ | |
| 56 | p-NO₂ | m-CF₃ | CH₃ | CH₃ | −C(O)−C₆H₁₃ | |
| 57 | p-OCCH₃ (p-OC(O)CH₃) | H | CH₃ | CH₃ | COC₆H₁₃ | oil |
| 58 | p-OCH₃ | H | CH₃ | CH₃ | −C(O)−C₆H₄−4-F | 153.2–158.8 |

TABLE 2-continued

[Structure: substituted benzamide with G, G' on phenyl ring; N=C linked to C(CF$_3$)$_2$ group and CH-NR$^6$R$^2$; NR$^1$]

| Ex. # | G | G' | R$^1$ | R$^6$ | R$^2$ | mp (°C.) |
|---|---|---|---|---|---|---|
| 59 | p-OCH$_3$ | H | CH$_3$ | CH$_3$ | —C(O)—C$_6$H$_4$—OCH$_3$ | 140.7–141.8 |
| 60 | p-F | H | CH$_3$ | CH$_3$ | —C(O)—C$_6$F$_4$ (tetrafluorophenyl) | 115–116 |
| 61 | p-C$_{17}$H$_{33}$CO$_2$ | H | CH$_3$ | CH$_3$ | —C(O)—C$_6$H$_{13}$-n | oil |
| 62 | p-CN | H | CH$_3$ | CH$_3$ | —C(O)—N(H)—C(CH$_3$)(phenyl) | ND |
| 63 | p-N(piperidine) | H | CH$_3$ | CH$_3$ | —C(O)—C$_6$H$_4$—N(piperidine) | 165.6 |
| 64 | p-OH | H | CH$_3$ | CH$_3$ | —C(O)—C$_6$H$_4$—CN | ND |
| 65 | p-CN | H | CH$_3$ | H | —C(O)—C$_6$H$_4$—CN | ND |
| 66 | p-CN | H | CH$_3$ | H | —C(O)—cyclohexyl | ND |
| 67 | p-F | H | CH$_3$ | H | —C(O)—N(H)—C$_6$H$_4$—CN | ND |
| 68 | p-F | H | CH$_3$ | H | —C(O)—cyclohexyl | 120 |
| 69 | p-CN | H | CH$_3$ | H | —C(O)—C$_6$H$_4$—F | ND (R-isomer) |

TABLE 2-continued

Structure: benzene ring with G and G' substituents, connected to C(=N-C(CF3)2-CH(NR2R6))(NR1)

| Ex. # | G | G' | R¹ | R⁶ | R² | mp (°C.) |
|---|---|---|---|---|---|---|
| 70 | p-CN | H | CH₃ | H | −C(=O)−C₆H₄−4-F | ND (S-isomer) |
| 71 | p-F | H | CH₃ | CH₂CH=CH₂ | −C(=O)−C₆H₄−4-F | 154.9 (HCl salt) |
| 72 | p-F | H | CH₃ | H | −C(=O)−C₆H₄−4-F | ND (S-isomer) |
| 73 | p-CN | H | CH₃ | CH₃ | −C(=O)−C₆H₄−4-CN | ND (R-isomer) |
| 74 | p-CN | H | CH₃ | CH₃ | −C(=O)−C₆H₄−4-CN | ND (S-isomer) |
| 75 | p-CN | H | CH₃ | CH₃ | −C(=O)−C₆H₄−4-CN | 181.1–181.8 (R-isomer H₂SO₄ salt) |
| 76 | p-CN | H | CH₃ | CH₃ | −C(=O)−C₆H₄−4-CN | 181.8–183.7 (S-isomer H₂SO₄ salt) |
| 77 | p-F | H | CH₃ | CH₃ | −C(=O)−C₆H₄−4-Br | 173.0–173.3 |
| 78 | p-C(=O)−OCH₃ | H | CH₃ | CH₃ | −C(=O)−C₆H₄−4-F | 162.4–163.7 |
| 79 | p-CN | H | CH₃ | CH₃ | −C(=O)−C₆H₄−4-O(CH₂)₃CH₃ | ND (R-isomer) |
| 80 | p-CN | H | CH₃ | CH₃ | −C(=O)−C₆H₄−4-O(CH₂)₃CH₃ | ND (S-isomer) |

TABLE 2-continued
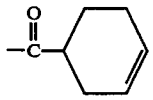
| Ex. # | G | G' | R¹ | R⁶ | R² | mp (°C.) |
|---|---|---|---|---|---|---|
| 81 | p-CN | H | CH₃ | CH₃ | 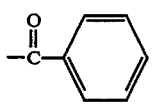 | 201.0–201.9 |
| 82 | p-CN | H | CH₃ | CH₃ |  | 209.9–210.9 |
| 83 | p-C(=N)OCH₃ | H | CH₃ | CH₃ | 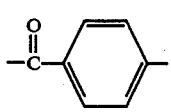 | 142.7–143.2 |
| 84 | p-F | H | CH₃ | CH₃ | 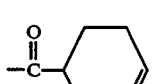 | 103–105 |
| 85 | p-F | H | CH₃ | CH₃ | 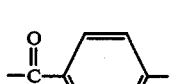 | ND (R-isomer) |
| 86 | p-F | H | CH₃ | CH₃ |  | ND (S-isomer) |
| 87 | p-F | H | CH₃ | CH₃ | 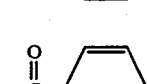 | 132–133.2 |
| 88 | p-SCH₃ | H | CH₃ | CH₃ |  | 186.6–187.7 |
| 89 | p-CN | H | CH₃ | CH₃ | 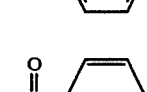 | 118 (d, HCl salt) |
| 90 | p-F | H | CH₃ | CH₃ | 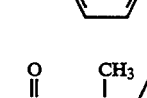 | 177.9 (isomer 1-R) |
| 91 | p-F | H | CH₃ | CH₃ |  | 101.0 (isomer 2-R) |

TABLE 2-continued

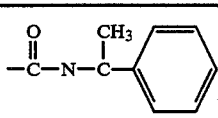

| Ex. # | G | G' | R¹ | R⁶ | R² | mp (°C.) |
|---|---|---|---|---|---|---|
| 92 | p-F | H | CH₃ | CH₃ | 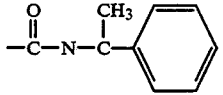 | ND (isomer 1-S) |
| 93 | p-F | H | CH₃ | CH₃ | 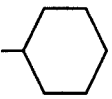 | ND (isomer 2-S) |

Notes.
Example 17: MS m/e 525; ¹H NMR(CDCl₃) δ 0.87(s, 3H, CH₃), 1.27(m, 16H, (CH₂)₈), 1.67(m, 2H, CH₂), 2.37(m, 2H, CH₂), 2.93(s, 6H, 2NCH₃), 6.63(s, 1H, CH), 7.17(m, 2H, H$_{arom}$), 7.63(m, 2H, H$_{arom}$).
Example 22: MS m/e 454; ¹H NMR(CDCl₃) δ 3.00(s, 3H, NCH₃), 3.20(s, 3H, NCH₃), 6.70(s, 1H, CH), 7.20(m, 4H, H$_{arom}$), 7.60(m, 2H, H$_{arom}$), 7.70(m, 2H, H$_{arom}$).
Example 23: MS m/e 438; ¹H NMR(CDCl₃) δ 2.97(s, 3H, NCH₃), 3.20(s, 3H, NCH₃), 6.57(s, 1H, CH), 6.73(s, 1H, CH), 7.23(m, 3H, H$_{arom}$), 7.67(m, 3H, H$_{arom}$).

TABLE 2.1

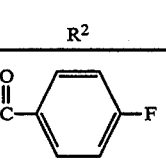

| Ex. # | Ar¹ | R¹ | R⁶ | R² | mp (°C.) |
|---|---|---|---|---|---|
| 95.1 |  | CH₃ | H |  | 137.9–140.4 |
| 95.2 |  | CH₃ | CH₃ |  | 125.9–126.9 |

EXAMPLE 96

Preparation of
2-[4,4-bis(trifluoromethyl)-2-(4-fluorophenyl)-4,5-dihydro-1-methyl-1H-imidazol-5-ylidene]-1-(4-fluorophenyl)-1-ethanone

Part A-1

To a solution of α,α-bis(trifluoromethyl)-4,5-bis(4-fluorophenyl)-1H-pyrrole-2-methanamine (4.0 g, 0.009 mole) in chloroform and methanol (1.5 l; 1:1) was added methylene blue (10 mg). Oxygen gas or air was bubbled through the solution while irradiating with a Tungsten lamp (400 watt) for 1 hour. 1M hydrochloric acid in ether (10 ml) was added to the reaction mixture and stirred for 1 hour at room temperature. The mixture was treated with saturated sodium carbonate solution (15 ml) and the organic layer was separated, concentrated, resuspended in ethyl acetate (200 ml), and washed with saturated ammonium chloride solution, saturated sodium chloride solution, dried over sodium sulfate (anhyd.) and evaporated under vacuum. The residue was purified by column chromatography, eluting with hexane-ethyl acetate (10:1) to give the 2-[4,4-bis(trifluoromethyl)-2-(4-fluorophenyl)-4,5-dihydro-1H-imidazol-5-ylidene]-1-(4-fluorophenyl)-1-ethanone (2.03 g, 49%).

Part A-2

To a solution of α,α-bis(trifluoromethyl)-4,5-bis(4-fluorophenyl)-1H-pyrrole-2-methanamine (5.0 g, 0.012 mole) in chloroform (100 mL) was added portionwise, m-chloroperbenzoic acid (MCPBA, 4.09 g, 0.024 mole). The reaction mixture was refluxed under nitrogen for one hour. Then additional MCPBA (2.05 g, 0.012 mole) was added and the mixture was refluxed for 1 hour. The solution was cooled to room temperature and poured into saturated sodium bicarbonate (200 ml). The organic layer was washed successively with saturated sodium bicarbonate solution, 10% sodium sulfite solution, water, and saturated sodium chloride solution, dried over magnesium sulfate and evaporated under vacuum. The residue was columned in silica gel eluted with hexane-ethyl acetate 20:1 then 10:1 to give the 2-[4,4-bis(trifluoromethyl)-2-(4-fluorophenyl)-4,5-dihydro-1H-imidazol-5-ylidene]-1-(4-fluorophenyl)-1-ethanone (1.02 g, 20%) as a yellow solid: mp 121°–123°; MS m/e 435 (M⁺+H); ¹H NMR (CDCl₃/TMS) δ 6.73(s,1H,C=CH), 7.17–7.30(m,4H,H$_{arom}$), 8.00–8.10(m,4H,H$_{arom}$), 11.80(s,1H,NH). Another product, N[2-(4-fluorophenyl)-4,5-dihydro-1-methyl-5,5-bis(trifluoromethyl)-1H-imidazol-5-yl]-N-methylacetamide (2.09 g, 56%) was also isolated as a solid: mp 114°–115°; MS m/e 437 (M⁺+H); ¹H NMR (CDCl₃/TMS) δ 2.57(s,2H,NH₂), 3.87(s,1H,NH), 6.77(s,1H,C=CH), 6.90–7.03(m,4H,H$_{arom}$), 7.23–7.40(m,2H,H$_{arom}$), 7.15–7.17(m,2H,H$_{arom}$).

Part B

Sodium hydride (80 mg, 2.0 mmole) 60% suspension in oil was washed with hexane and then it was suspended in anhydrous dimethyl formamide (5 mL). To this suspension was added portionwise 2-[4,4-bis(trifluoromethyl)-2-(4-fluorophenyl)-4,5-dihydro-1H-imidazol-5-ylidene]-1-(4-fluorophenyl)-1-ethanone (0.43 g, 1 mmole) and the mixture was allowed to stir at room temperature for one hour. Iodomethane (0.28 g, 2 mmole) was added dropwise and the reaction mixture was allowed to stir at room temperature overnight. The reaction mixture was poured into water and extracted with ether. The organic layer was washed successively with water and saturated sodium chloride solution, dried over anhydrous magnesium sulfate and concentrated. The residue was recrystallized from dichloromethane-hexane to give the title compound (0.20 g, 91%) as a crystalline solid: mp 128°–129°; MS m/e 449(M++H); $^1$H NMR (CDCl$_3$/TMS) δ 3.17(s,3H,NCH$_3$), 6.67(s,1H,C=CH), 7.13–7.30(m,4H-,H$_{arom}$), 7.77–7.87(m,2H,H$_{arom}$), 7.93–8.07(m,2H,H$_{arom}$).

The compound of Example 96, and other compounds of Formula (I) wherein X is CH which have been prepared or could be prepared using the same or similar synthetic methods, are listed in Table 3.

TABLE 3

| Ex. # | G | G' | G'' | G''' | R$^1$ | R$^6$ | mp (°C.) |
|---|---|---|---|---|---|---|---|
| 96 | p-F | H | p-F | H | CH$_3$ | H | 128–129 |
| 97 | p-OCH$_3$ | H | p-OCH$_3$ | H | CH$_3$ | H | ND |
| 98 | p-F | H | p-OCH$_3$ | H | CH$_3$ | H | ND |
| 99 | p-OC$_4$H$_9$ | H | p-OC$_4$H$_9$ | H | CH$_3$ | H | ND |
| 100 | p-CN | H | p-CN | H | CH$_3$ | H | |
| 101 | p-CN | H | p-F | H | CH$_3$ | H | |
| 102 | p-CF$_3$ | H | p-CF$_3$ | H | CH$_3$CH$_2$ | H | |
| 103 | p-CH$_3$ | H | p-CH$_3$ | H | CH$_3$CH$_2$ | H | |
| 104 | p-Cl | H | p-Cl | H | H | H | |
| 105 | p-Cl | m-Cl | p-Cl | m-Cl | CH$_2$=CHCH$_2$ | H | |
| 106 | p-F | o-F | p-F | o-F | CH$_3$ | H | |
| 107 | p-N$_3$ | H | p-N$_3$ | H | CH$_3$CH$_2$ | H | |
| 108 | p-N$_3$ | H | p-F | H | CH$_2$=CHCH$_2$ | H | |
| 109 | p-N(piperidinyl) | H | p-N(piperidinyl) | H | CH$_3$ | H | |
| 110 | p-N(piperidinyl) | H | p-F | H | CH$_3$ | H | |
| 111 | p-COCH$_3$ | H | p-COCH$_3$ | H | CH$_3$CH$_2$ | H | |
| 112 | p-NO$_2$ | H | p-NO$_2$ | H | CH$_3$ | H | |
| 113 | p-NO$_2$ | m-Cl | p-NO$_2$ | m-Cl | H | H | |
| 114 | p-NO$_2$ | m-CN | p-NO$_2$ | m-CN | CH$_3$CH$_2$ | H | |
| 115 | p-N(morpholinyl) | H | p-N(morpholinyl) | H | CH$_3$ | H | |
| 116 | p-N(CH$_3$)$_2$ | H | p-F | H | CH$_2$=CHCH$_2$ | H | |
| 117 | p-F | H | p-N(CH$_3$)$_2$ | H | CH$_3$ | H | |
| 118 | p-SO$_2$CH$_3$ | H | p-SO$_2$CH$_3$ | H | CH$_3$ | H | |
| 119 | p-N(CH$_3$)$_2$→O | H | p-F | H | CH$_2$CH$_3$ | H | |

TABLE 3-continued

| Ex. # | G | G' | G'' | G''' | R$^1$ | R$^6$ | mp (°C.) |
|---|---|---|---|---|---|---|---|
| 119.1 | p-F | H | p-F | H | CH$_3$ | CH$_3$ | 172–176 |
| 119.2 | p-F | H | p-OCH$_3$ | H | CH$_3$ | CH$_3$ | ND |
| 119.3 | p-N(piperidinyl) | H | p-N(piperidinyl) | H | CH$_3$ | H | 209–211 (E-isomer) |
| 119.4 | p-N(piperidinyl) | H | p-N(piperidinyl) | H | CH$_3$ | H | 138–139 (Z-isomer) |
| 119.5 | p-F | H | p-N(piperidinyl) | H | CH$_3$ | H | 154.5–155.5 (Z-isomer) |

Notes.

Example 97: MS m/e 473; $^1$H NMR(CDCl$_3$) δ 3.17(s, 3H, NCH$_3$), 3.87(2s, 6H, OCH$_3$), 6.63(s, 1H, CH), 7.00(m, 4H, H$_{arom}$), 7.73(d, 2H, J=10Hz, H$_{arom}$), 7.93(d, 2H, J=10Hz, H$_{arom}$).

Example 98: MS m/e 461; $^1$H NMR(CHCl$_3$) δ 3.17(s, 3H, NCH$_3$), 3.90(s, 3H, OCH$_3$), 6.63(s, 1H, CH), 7.00(d, 2H, J=10Hz, H$_{arom}$), 7.23(m, 2H, H$_{arom}$), 7.93(m, 2H, H$_{arom}$), 8.00(d, 2H, J=10Hz, H$_{arom}$).

Example 99: Ms m/e 557; $^1$H NMR(CHCl$_3$)δ 0.93(m, 6H, 2CH$_3$), 1.50(m, 4H, 2CH$_2$), 1.60(m, 4H, 2CH$_2$), 3.17(s, 3H, NCH$_3$), 4.03(m, 4H, 2OCH$_2$) 6.60(s, 1H, CH), 6.97(m, 4H, H$_{arom}$), 7.00(d, 2H, J=10Hz, H$_{arom}$), 7.93(d, 2H, J=10Hz, H$_{arom}$).

EXAMPLE 120

1-(4-fluorophenyl-2-[2-(4-fluorophenyl)-4,5-dihydro-1-methyl-4,4-bis(trifluoromethyl)-1H-imidazol-5-yl]-ethanone To a refluxing solution of 2-[4,4-bis(trifluoromethyl)-2-(4-fluorophenyl)-4,5-dihydro-1-methyl-1H-imidazo-5-ylidene]-1-(4-fluorophenyl)-1-ethanone (100 mg, 0.22 mmole) in acetic acid (15 ml) was added zinc dust (3.7 g, 56.6 mmole) over a period of 5 minutes. After 10 minutes, the mixture was filtered and washed with hot acetic acid. The filtrate was diluted with saturated sodium bicarbonate solution (120 ml) and extracted with ether (4×50 ml). The combined organic layer was washed with saturated sodium chloride solution, dried with magnesium sulfate (anhyd.) and evaporated under vacuum to give the title compound (78 mg, 79%) as colorless needles, mp 145°–146.6° C.; $^1$H NMR (CDCl$_3$/TMS) δ 2.79(s,3H,CH$_3$), 2.54–2.60(m,2H,CH$_2$), 5.89–5.97(m,1H,CH); 7.10–7.30(m,4H,H$_{arom}$), 7.55–7.68(m,2H,H$_{arom}$), 8.02–8.09(m,2H,H$_{arom}$). The compound of Example 120–120.2, and other compounds of formula (I) wherein X is CH$_2$ which have been prepared or could be prepared using the same or similar synthetic methods, are listed in Table 4.

TABLE 4

| Ex. # | G | G' | R$^1$ | R$^6$ | R$^2$ | mp (°C.) |
|---|---|---|---|---|---|---|
| 120 | p-F | H | CH$_3$ | H | C(O)-C$_6$H$_4$-F(p) | 145–146 |

TABLE 4-continued

[Structure: A substituted benzene ring with G and G' substituents, connected to a C=N group, linked to N-R¹, with a chain: N=C-CH(R²)-CH(H)-C(CF₃)(CF₃) and R⁶ substituent]

| Ex. # | G | G' | R¹ | R⁶ | R² | mp (°C.) |
|-------|------|----|-----------|-----|-----------------------------------------|--------------------------|
| 120.1 | p-F | H | CH₂CH₃ | H | -C(=O)-C₆H₄-4-F | ND |
| 120.2 | p-F | H | CH₃ | H | -C(=O)-C₆H₄-4-CN | ND |
| 120.3 | p-F | H | CH₃ | CH₃ | -C(=O)-C₆H₄-4-OCH₃ | ND (2S-isomer) |
| 120.4 | p-F | H | CH₃ | CH₃ | -C(=O)-C₆H₄-4-OCH₃ | ND (2R-isomer HCl salt) |
| 120.5 | p-OCH₃ | H | CH₃ | CH₃ | -C(OH)(CH₃)-C₆H₄-4-OCH₃ | ND |
| 120.6 | p-OCH₃ | H | CH₃ | H | -C(OH)(CH₃)-C₆H₄-4-OCH₃ | 151–152 (2S-isomer) |
| 120.7 | p-OCH₃ | H | CH₃ | H | -C(OH)(CH₃)-C₆H₄-4-OCH₃ | ND (2R-isomer; HCl salt) |
| 120.8 | p-F | H | CH₂CH=CH₂ | H | -C(=O)-C₆H₄-4-F | ND |
| 120.9 | p-OCH₃ | H | CH₃ | H | -C(=O)-C₆H₄-4-OCH₃ | 188.5 |
| 120.10 | p-F | H | CH₂CH₃ | H | -CH(OH)-C₆H₄-4-F | 185–186 (S-isomer) |
| 120.11 | p-F | H | CH₂CH₃ | H | -CH(OH)-C₆H₄-4-F | 168–170 (R-isomer) |

TABLE 4-continued

[Structure: Imidazoline with F₃C, CF₃ groups, N=C linkage to phenyl substituted with G and G', with N-R¹ and CH-R² side chain with R⁶]

| Ex. # | G | G' | R¹ | R⁶ | R² | mp (°C.) |
|---|---|---|---|---|---|---|
| 120.12 | p-F | H | CH₂CH₃ | H | —C(OH)— linked to 4-F-phenyl | ND |
| 120.13 | p-N | H | CH₃ | H | —C(=O)— linked to 4-(piperidinyl)phenyl | ND |

EXAMPLE 121

Preparation of
[4,4-(bis(trifluoromethyl)-2-(4-methoxyphenyl)-4,5-dihydro-1H-imidazol-5-ylidene]-carbamic acid-(4-methoxyphenyl)-ester To a solution of α,α-bis(tri-fluoromethyl)-4,5-bis(4-methoxyphenyl)-1-methyl-1H-imidazol-2-methanamine (0.40 g, 87 mmole) in chloroform (10 mL) was added portionwise, m-chloroperbenzoic acid (0.75 g, 4.30 mmole). The reaction mixture was refluxed under nitrogen for two hours. The solution was cooled to room temperature and poured into saturated sodium bicarbonate (100 mL). The organic layer was washed successively with saturated sodium bicarbonate solution, 10% sodium sulfite solution, water, and saturated sodium chloride solution, dried over magnesium sulfate and evaporated under vacuum. The residue was triturated with hexane to give the title compound (0.20 g, 40%) as a white solid: mp 141°-142°; MS m/e 489 (M⁺+H); ¹H NMR (CDCl₃/TMS) δ 3.33(s,3H,OCH₃), 3.93(s,3H,OCH₃), 6.85-7.20(m,6H,H$_{arom}$), 7.67-7.73(m,2H,H$_{arom}$); Anal. Calcd for C₂₁H₁₇N₃O₄F₆: C,51.54; H,3.50; Found: C,50.92; H,3.68.

EXAMPLE 122

Preparation of
[4,4-bis(trifluoromethyl)-2-(4-methylphenyl)-4,5-dihydro-1H-imidazol-5-ylidene]-carbamic acid-(4-methylphenyl)-ester To a solution of α,α-bis(trifluoromethyl)-4,5-bis(4-methylphenyl)-1-methyl-1H-imidazol-2-methanamine (1.0 g, 2.3 mmole) in chloroform (10 mL) was added portionwise, m-chloroperbenzoic acid (1.20 g, 7 mmole). The reaction mixture was refluxed under nitrogen for two hours. The solution was cooled to room temperature and poured into saturated sodium bicarbonate (100 mL). The organic layer was washed successively with saturated sodium bicarbonate solution, 10% sodium sulfite solution, water, and saturated sodium chloride solution, dried over magnesium sulfate and evaporated under vacuum. The residue was triturated with petroleum ether to give the title compound (0.15 g, 14%) as a solid: mp 161°-163°; MS m/e 458 (M⁺+H); ¹H NMR (CDCl₃/TMS) δ 2.43 (s,6H,CH₃), 3.06(s,3H,NCH₃), 7.23-7.40(m,4H,H$_{arom}$), 7.50-7.63(m,2H,H$_{arom}$), 7.87-7.93(m,2H,H$_{arom}$).

The compounds of Examples 120 and 121, and other compounds of Formula (I) wherein a is a double bond and Ar² is CO₂Ar which could be prepared using the same or similar synthetic methods, are listed in Table 4.

TABLE 5

[Structure: Ar¹—C=N ring with CF₃, CF₃ groups, =N—C(=O)—O—Ar², with N-R¹]

| Ex. # | Ar¹, Ar² | R¹ | mp (°C.) |
|---|---|---|---|
| 121 | 4-methoxyphenyl | CH₃ | 141-142 |
| 122 | 4-methylphenyl | CH₃ | 161-163 |

EXAMPLE 123

Preparation of
2-(4-fluorophenyl)-3,5-dihydro-3-methyl-4,4-bis(trifluoromethyl)-4H-imidazol-4-one A solution of N-[4,4-bis(trifluoromethyl)-2-(4-fluorophenyl)-4,5-dihydro-1-methyl-1H-imidazol-5-ylidene]-4-fluorophenylbenzamide (1.1 g, 2.3 mmole) in diethyl ether was eluted to the center of a basic alumina (III) column with ether at room temperature. After two hours, the material was eluted from the column with ethyl acetate and the crude product was purified by column chromatography with hexane-ethyl acetate (10:1) to give the title compound in quantitative yield (0.80 g) as a white solid: mp 59°-61°. MS m/e 329

(M++H). $^1$H NMR (CDCl$_3$/TMS) δ 3.25(s,3H,NCH$_3$), 7.25(m,2H,H$_{arom}$), 7.80(m,2H,H$_{arom}$).

TABLE 6

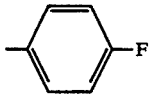

| Ex. # | Ar$^1$ | R$^1$ | mp (°C.) |
|---|---|---|---|
| 123 | 4-F-C$_6$H$_4$ | CH$_3$ | 59–61 |

Utility

The compounds of the invention are effective antiatherosclerotic agents that act in a variety of ways. The compounds may be inhibitors of the enzyme acyl CoA:-cholesterol acyl transferase (ACAT). Inhibition of ACAT has a variety of antiatherosclerotic effects, including inhibiting esterification and transport of cholesterol across the intestinal wall. In addition, by inhibiting cholesterol ester formation, the compounds may be useful in preventing the formation of cholesterol ester rich macrophages (foam cells) in the arterial wall. Foam cells are a source of the large quantity of cholesterol ester found in atheromatous lesions, as compared to the surrounding undiseased tissue. Other compounds of the invention may be inhibitors of cholesterol biosynthesis in the liver. Some compounds of the invention are both ACAT inhibitors and inhibitors of cholesterol biosynthesis.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rates weighing 150–300 g were fed rat chow ad libitum. The animals were fasted for twenty-four hours prior to being sacrificed by decapitation. The livers were perfused in situ with 50 ml of cold 0.25M sucrose, excised and homogenized in three volumes of 0.1M phosphate buffer, pH 7.4, that contained 0.5 mM EDTA (ethylenediaminetetraacetic acid), 1.0 mM glutathione, 0.25M sucrose and 20 mM leupeptin. Microsomes were obtained by differential centrifugation; the supernatant from an initial spin at 15,000×g for 15 minutes was centrifuged at 105,000×g for 1 hour to pellet the microsomes. The microsomes were suspended in homogenization buffer, reisolated by centrifugation, and stored at −70° C. Microsomes were used within one month of preparation.

The control assay in a final volume of 200 μl consisted of 200 μg of microsomal protein, 75 μM $^{14}$C-oleoyl-CoA (10,000 dpm/nmol) in 0.1M phosphate, pH 7.4, that contained 1 mM glutathione. Compounds were added in 5–10 μl of DMSO (dimethyl sulfoxide or ethanol) and additional controls were run with DMSO or ethanol only. All components, except the oleoyl-CoA, were preincubated for 15 min. at 37° C. prior to the initiation of the reaction by the addition of oleoyl CoA. The assay was terminated after 10 min by the addition of 4 ml of chloroform:methanol (2:1, v/v). 20,000 dpm of $^3$H-cholesteryl oleate and 10 μg of unlabeled cholesteryl oleate and oleic acid were added as an internal standard and carrier, respectively. After allowing 10 min. for lipid extraction, 0.8 ml of deionized water was added to separate the solution into two phases. The lower chloroform phase was collected, dried under nitrogen and resuspended in 100 μl of chloroform. The sample containing the neutral lipids was spotted onto a Gelman ITLC-SA polysilicic acid gel-impregnated sheet, which was developed using a hexane: diethyl ether: acetic acid (170:30:1 v/v/v) mobile phase. The lipids were visualized by their interaction with iodine vapor and the cholesteryl ester spot was scraped into a scintillation vial and counted. The specific activity of ACAT in the control incubation averaged 260 pmol/-min/mg microsomal protein. The inhibition of ACAT activity by the compounds is shown in Table 7; the data are expressed as the concentration at which ACAT activity is inhibited by 50% (IC$_{50}$).

B. Assay of the Inhibition of Cholesterol Esterification in Mammalian Cells

The esterification of cholesterol was determined in the murine macrophage-like cell line J744.A1. Cells were seeded in 35 mm wells at a density of 300,000 cells per well in 2 mls of Dulbecco's Modified Eagle Medium (DMEM) supplemented with 10% fetal bovine serum (FBS). Cells were incubated at 37° C. in an atmosphere of 5% CO$_2$ and 93% humidity. After 24 hours the media was changed to 0.68 mls 10% FBS-DMEM containing 34 μg of acetylated human low density lipoprotein (ac-LDL) to increase the intracellular concentration of cholesterol and promote esterification. At 41 hours, various inhibitors were added to the cells in DMSO (10 μl/ml maximum). At 43 hours, the cells were pulsed with 0.1 mM $^{14}$C oleic acid (10,000 dpm/nmol) complexed with BSA (bovine serum albumin) to follow cholesterol ester formation. The experiment was terminated at 45 hours by washing the monolayers 3 times with 3 ml of Tris-buffered saline at 4° C. The lipids were extracted by incubating the monolayers with 1.5 ml of hexane: isopropanol (3:2, v/v) for 30 min. under gentle agitation. During this period, 10,000 dpm $^3$H-cholesteryl linoleate and 10 μg of cholesteryl oleate were added as an internal standard and carrier respectively. The organic solvent was remoted and the cells were washed with an additional 1.0 ml of hexane: isopropanol which was combined with the original extract. The cells were allowed to dry overnight, digested with 1.5 ml of 0.2 N sodium hydroxide for 1 hour and an aliquot of the solubilized protein used for protein determination using the Lowry method. The organic extract was taken to dryness, the residue resuspended in 100 μl of chloroform and a lipids separated on silica gel impregnated glass fiber plates using a hexane: diethylether: acetic acid (170:30:1, v/v/v) solvent system. Individual lipids were visualized with iodine and the cholesteryl ester spot cut out and transferred to scintillation vials to determine the amount of radioactivity. The conversion of oleic acid to cholesteryl ester in the control averaged 0.54 mmol/hr/mg protein and was increased upon the addition of ac-LDL to about 10.69±0.69 mmol/hr/mg protein. The inhibition of esterification by the compounds is shown in Table 8; the data are expressed as the concentration at which ACAT activity is inhibited by 50% (IC$_{50}$).

TABLE 7

Inhibition of In Vitro Hepatic ACAT Activity By Various Compounds

| Compound of Example | In Vitro ACAT IC$_{50}$ |
|---|---|
| 2 | 20 μM |
| 5 | 20 μM |
| 10 | 41 μM |
| 10A | 22 μM |
| 11 | 2 μM |
| 12 | 6 μM |
| 13 | 4 μM |
| 14 | 8 μM |
| 15 | 17 μM |
| 16 | 2 μM |
| 17 | 6 μM |
| 18 | 4 μM |
| 25 | 41 μM |
| 26 | 45 μM |
| 27 | 3 μM |
| 28 | 22 μM |
| 29 | 16 μM |
| 30 | 6 μM |
| 34 | 9 μM |
| 31 | 10 μM |
| 32 | 2 μM |
| 33 | 10 μM |
| 96B | 19 μM |
| 121 | 64 μM |
| 122 | 49 μM |
| 123 | >100 μM |
| Q | 1.91 μM |
| R | 2.0 μM |

TABLE 8

Inhibition of Cholesterol Esterification in Macrophage by Various Compounds

| Cholesterol of Example | Compound Esterification (IC$_{50}$) |
|---|---|
| 2 | >100 μM |
| 5 | 62 μM |
| 10A | 105 μM |
| 11 | 14 μM |
| 13 | 18 μM |
| 14 | 18 μM |
| 15 | 11 μM |
| 16 | 17 μM |
| 25 | 98 μM |
| 26 | 96 μM |
| 27 | 16 μM |
| 31 | 13 μM |
| 32 | 17 μM |
| 33 | 13 μM |
| R | 13 μM |
| Q | 34 μM |

Dosage Forms

The compounds of the present invention can be administered using a variety of pharmaceutically acceptable dosage forms known in the art. The active ingredient will normally be administered orally and can be supplied in solid dosage forms such as dry powders, granules, tablets, capsules, or bars, or in liquid dosage forms, such as syrups or aqueous suspensions. The active ingredient can be administered alone, but is generally administered with a pharmaceutical carrier. These compounds may be administered in combination with other active ingredients.

In their therapeutic use as antihypercholesterolemic and/or antiatherosclerotic agents, the compounds of the invention are administered to the patient at dosage levels of 7 to 7000 mg per day. For a normal male adult human of approximately 70 kg of body weight, this translates into a dosage of 1 to 100 mg per kilogram body weight per day. The dosage administered will, of course, vary depending upon known factors such as the age, health, and weight of the recipient nature and extent of symptoms, kind of concurrent treatment, frequency of treatment, and the effect desired.

The various classes of pharmaceutical preparations are discussed in *Remington's Pharmaceutical Sciences*, a standard reference text in this field. See also, the USP/NF for solvents and other pharmaceutical necessities suitable for use in pharmaceutical dosage forms. The teaching of these references is hereby incorporated by reference. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

Syrup

| | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension

| | Wt. % |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthum gum is slowly added into distilled water before adding the active ingredient and the rest of the formulation ingredients. The final suspension is passed through a homogenizer to assure the elegance of the final products.

Resuspendible Powder

| | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

|  | Wt. % |
|---|---|
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packing container and cooled down to form the gel.

Semi-Solid Paste

|  | Wt. % |
|---|---|
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution.

Sodium saccharin and the rest of the formulation ingredients are added to the suspension while it is still warm. The suspension is homogenized and then filled into suitable containers.

Emulsifiable Paste

|  | Wt. % |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

What is claimed is:

1. A compound of the fomula:

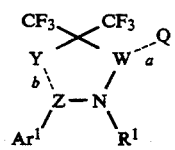

wherein $Ar^1$ is phenyl optionally mono-, di- or tri-substituted with a member of the group consisting of —F, —Cl, —Br, —I, —CF$_3$, —CONH$_2$, —NO$_2$, —CHO, —CO$_2$Et, —CN, —O$_2$CR$^9$, —SCH$_3$, —SCF$_3$, —SO$_2$CF$_3$, SO$_2$CH$_3$, 5-tetrazolyl, —N(O)(CH$_3$)$_2$, OH, C$_1$–C$_7$ alkoxy, N-piperidyl, C$_1$–C$_{10}$ alkyl, C$_3$–C$_7$ cycloalkyl, or C$_3$–C$_{10}$ substituted cycloalkyl, or $Ar^1$ may be C$_1$–C$_{10}$ alkyl, C$_3$–C$_7$ cycloalkyl or C$_4$–C$_7$ substituted cycloalkyl with substituents selected from the group defined above, where $R^9$ is H or alkyl, alkenyl, or alkynyl of 1 to 20 carbon atoms;

a and b are independently a single or double bond;

Q is O or X—$R^2$ wherein X is bonded to W, provided that when Q is O, a is a double bond;

X is N, NR$^6$, CH, CHR$^6$, or S, R$^6$ is H or C$_1$–C$_3$ alkyl, alkenyl, or alkynyl;

W is C or CH, provided that when a is a single bond, X is NR$^6$ or CH$_2$ and W is CH, and when a is a double bond, X is N or CH and W is C;

Y is N or NR$^7$ wherein R$^7$ is H or C$_1$–C$_3$ alkyl;

Z is C or CH, provided that when b is a single bond, Y is NR$^7$ and Z is CH, and when b is a double bond, Y is N and Z is C;

$R^1$ is H or C$_1$–C$_3$ alkyl, alkenyl, or alkynyl;

$R^2$ is C$_4$ to C$_{15}$ alkyl, C$_4$ to C$_{15}$ alkynyl, or C$_4$ to C$_{15}$ alkenyl, which may be straight, branched or cyclic, optionally with a terminal COOH or OH group; or $R^2$ is COR$^3$ where R$^3$ is C$_1$ to C$_{15}$ alkyl, C$_2$ to C$_{15}$ alkynyl, or C$_2$ to C$_{15}$ alkenyl, which may be straight, branched, or cyclic, optionally with a terminal COOH or OH group; or $R^2$ is COAr$^2$, CH$_2$Ar$^2$, CO$_2$Ar$^2$, CONR$^8$Ar$^2$, where R$^8$ is H or C$_1$–C$_3$ alkyl, SO$_2$Ar$^2$, SO$_2$NHAr$^2$, or SO$_2$R$^3$;

$Ar^2$ is phenyl optionally substituted with one or more of a member of the group consisting of —F, —Cl, —Br, —I, —CF$_3$, p—NO$_2$, —CN, —CHO, —N$_3$, C$_1$–C$_7$ alkyl, C$_1$–C$_7$ alkoxy, phenyl, or NR$^4$R$^5$, where R$^4$ and R$^5$ are independently H or C$_1$–C$_3$ alkyl, or R$^4$ and R$^5$ taken together represent —(CH$_2$)$_3$—, —(CH$_2$)$_4$— or —(CH$_2$)$_5$—, or $Ar^2$ is C$_2$–C$_{11}$ alkyl, alkenyl or alkynyl which may be straight or branched or $Ar^2$ is a C$_3$–C$_{11}$ carbocycle which may be saturated, unsaturated or aromatic; provided that when X is CH or CH$_2$ and $R^2$ is COAr$^2$, $Ar^1$ and $Ar^2$ are independently, phenyl or substituted phenyl and when X is CH$_2$, $R^2$ is COAr$^2$, CH$_2$Ar$^2$, or CO$_2$Ar$^2$; or a resolved optical antipode of any chiral form thereof; or a pharmaceutically acceptable salt thereof.

2. A compound of claim 1 wherein:

$Ar^1$ is phenyl, optionally mono-, di-, or tri-substituted with a member of the group consisting of —F, —Cl, —Br, —I, —CN, —CF$_3$, —CONH$_2$, —OH, —NO$_2$, 5-tetrazol, C$_1$–C$_7$ alkoxy, N-piperidyl, —O$_2$CR$^9$, where R$^9$ is C$_1$–C$_{20}$ alkyl, alkenyl, or alkynyl, or $Ar^1$ is cyclohexyl;

Q is O or X—$R^2$ wherein X is bonded to W, provided that when Q is O, a is a double bond;

X is N, NR$^6$, CH, CHR$^6$, or S, and R$^6$ is H, or C$_1$–C$_3$ alkyl, alkenyl, or alkynyl;

W is C or CH, provided that when a is a single bond, X is NR$^6$ or CH$_2$ and W is CH, and, when a is a double bond, X is N or CH and W is C;

Y is N or NR$^7$ wherein R$^7$ is H or CH$_3$;

Z is C or CH, provided that when b is a single bond, Y is NR$^7$ and Z is CH, and when b is a double bond, Y is N and Z is C;

$R^1$ is H or C$_1$–C$_3$ alkyl, alkenyl, or alkynyl;

63

$R^2$ is $COAr^2$, $CH_2Ar^2$, $CO_2Ar^2$, or $CONR^8Ar^2$, wherein $R^8$ is H or $C_1$–$C_3$ alkyl, and $Ar^2$ is phenyl, optionally substituted with one or more of a member of the group consisting of —F, —Cl, —Br, —I, —$CF_3$, —$N_3$, phenyl, $C_1$–$C_7$ alkyl, $C_1$–$C_7$ alkoxy, p—$NO_2$, —CHO, —CN, or $NR^4R^5$ where $R^4$ and $R^5$ are independently H, or $C_1$–$C_3$ alkyl, or $R^4$ and $R^5$ taken together represent —$(CH_2)_3$—, —$(CH_2)_4$ or —$(CH_2)_5$—, or $Ar^2$ is $C_2$–$C_{11}$ alkyl, alkenyl or alkynyl which may be straight or branched or $Ar^2$ is a $C_3$–$C_{11}$ carbocycle which may be saturated, unsaturated or aromatic;

3. A compound of claim 1 wherein:

$Ar^1$ is phenyl optionally monosubstituted with a member of the group consisting of —F, —Cl, —Br, —CN, —$CF_3$, —OH, $C_1$–$C_7$ alkoxy, —$NO_2$, —$CONH_2$, N-piperidyl, $CH_3$, or —$O_2CR^9$ where $R^9$ is $C_1$–$C_{20}$ alkyl, alkenyl, or alkynyl, or $Ar^1$ is cyclohexyl;

Q is X—$R^2$ wherein X is bonded to W;

X is $NR^6$ or $CH_2$, and $R^6$ is H, $C_1$–$C_3$ alkyl, alkenyl, or alkynyl;

W is CH;

Y is N;

Z is C;

$R^1$ is H, $CH_3$, or $C_2H_5$; and $R^2$ is $COAr^2$ or $CONR^8Ar^2$, wherein $R^8$ is H or $C_1$–$C_3$ alkyl; and $Ar^2$ is phenyl optionally monosubstituted with a member of the group consisting of —F, —Cl, —Br, —CN, —$CF_3$, $C_1$–$C_7$ alkyl, $C_1$–$C_4$ alkoxy, p—$NO_2$, phenyl, N-piperidyl, or dimethylamino, or $Ar^2$ is $C_6$–$C_{11}$ alkyl, which may be straight or branched.

4. A compound of claim 1 wherein:

$Ar^1$ is phenyl optionally mono-p-substituted with a member of the group consisting of —F, —Cl, —Br, —CN, —OH, —$OCH_3$, N-piperidinyl, —$CONH_2$ or $O_2CR^9$, where $R^9$ is $C_1$–$C_{20}$ alkyl, alkenyl, or alkynyl;

Q is X—$R^2$ wherein X is bonded to W;

X is $NR^6$ or $CH_2$, and $R^6$ is H or $C_1$–$C_3$ alkyl, alkenyl, or alkynyl;

W is CH;

Y is N;

Z is C;

$R^1$ is $CH_3$;

$R^2$ is $COAr^2$ or $CONR^8Ar^2$, wherein $R^8$ is H or $C_1$–$C_3$ alkyl; and $Ar^2$ is phenyl, optionally mono- p-substituted with a member of the group consisting of —F, —Cl, phenyl, $C_1$–$C_4$ alkyl, $C_1$–$C_4$ alkoxy, —CN, p—$NO_2$, N-piperidyl or $Ar^2$ is $C_6$–$C_{11}$ alkyl, which may be straight or branched.

5. The compound of claim 1 which is N-[4,4-bis(trifluoromethyl)-2-(4-fluorophenyl)-4,5-dihydro-1-methyl-1H-imidazol-5-yl]-4-butoxy-N-methylbenzamide, or a pharmaceutically acceptable salt thereof.

6. The compound of claim 1 which is N-[4,4-bis(trifluoromethyl)-2-(4-fluorophenyl)-4,5-dihydro-1-methyl-1H-imidazol-5-yl]-4-(1,1-dimethylethyl)-N-methylbenzamide, or a pharmaceutically acceptable salt thereof.

7. The compound of claim 1 which is N-[4,4-bis(trifluoromethyl)-2-(4-fluorophenyl)-4,5-dihydro-1-methyl-1H-imidazol-5-yl]-N-methyl-4-nitrobenzamide, or a pharmaceutically acceptable salt thereof.

8. The compound of claim 1 which is N-[4,4-bis(trifluoromethyl)-2-(4-fluorophenyl)-4,5-dihydro-1-meth-yl-1H-imidazol-5-yl]-4-(1-piperidinyl) benzamide, or a pharmaceutically acceptable salt thereof.

9. The compound of claim 1 which is N-[4,4-bis(trifluoromethyl)-2-(4-fluorophenyl)-4,5-dihydro-1-methyl-1H-imidazol-5-yl]-4-fluorophenyl-N-methylbenzamide, or a pharmaceutically acceptable salt thereof.

10. The compound of claim 1 which is N-[4,4-bis(trifluoromethyl)-4,5-dihydro-1-methyl-2-[4-(1-piperidinyl)phenyl]-1H-imidazol-5-yl]-4-fluorobenzamide, or a pharmaceutically acceptable salt thereof.

11. The compound of claim 1 which is N-[4,4-bis(trifluoromethyl)-2-(4-fluorophenyl)-4,5-dihydro-1-methyl-1H-imidazol-5-yl]-N-methylheptanamide, or a pharmaceutically acceptable salt thereof.

12. The compound of claim 1 which is N-[4,4-bis(trifluoromethyl)-2-(4-fluorophenyl)-4,5-dihydro-1-methyl-1H-imidazol-5-yl]-4-ethoxybenzamide, or a pharmaceutically acceptable salt thereof.

13. The compound of claim 1 which is N-[4,4-bis(trifluoromethyl)-2-(4-fluorophenyl)-4,5-dihydro-1-methyl-1H-imidazol-5-yl]-4-methoxy-N-methylbenzamide, or a pharmaceutically acceptable salt thereof.

14. The compound of claim 1 which is N-[4,4-bis(trifluoromethyl)-2-(4-fluorophenyl)-4,5-dihydro-1-methyl-1H-imidazol-5-yl]-N-methyl-[1,1'-biphenyl]-4-carboxamide, or a pharmaceutically acceptable salt thereof.

15. The compound of claim 1 which is N-[4,4-bis(trifluoromethyl)-2-(4-fluorophenyl)-4,5-dihydro-1-methyl-1H-imidazol-5-yl]-N'-2,4-difluorophenyl-N-methylurea, or a pharmaceutically acceptable salt thereof.

16. The compound of claim 1, which is N-[4,4-bis(trifluoromethyl)-4,5-dihydro-1-methyl-2-[4-(1-piperidinyl)phenyl]-1H-imidazo-5-yl]-N-methylheptanamide, or a pharmaceutically acceptable salt thereof.

17. The compound of claim 1 which is N-[4,4-bis(trifluoromethyl)-2-(4-methoxyphenyl)-4,5-dihydro-1-methyl-1H-imidazol-5-yl]-N,5-dimethylhexanamide, or a pharmaceutically acceptable salt thereof.

18. The compound of claim 1 which is N-[4-4-bis(trifluoromethyl)-2-(4-fluorophenyl)-4,5-dihydro-1-methyl-1H-imidazol-5-yl]-N'-4-isopropylphenyl-N-methylurea, or a pharmaceutically acceptable salt thereof.

19. The compound of claim 1 which is N-[4,4-bis(trifluoromethyl)-2-(4-fluorophenyl)-4,5-dihydro-1-methyl-1H-imidazol-5-yl]-N,5-dimethyl-hexanamide, or a pharmaceutically acceptable salt thereof.

20. The compound of claim 1 which is N-[4,4-bis(trifluoromethyl)-2-(4-fluorophenyl)-4,5-dihydro-1-methyl-1H-imidazol-5-yl]-N'-octyl-N-methylurea, or a pharmaceutically acceptable salt thereof.

21. The compound of claim 1 which is 1-(4-cyanophenyl)-2-[2-(4-fluorophenyl)-4,5-dihydro-1-methyl-4,4-bis(trifluoromethyl)-1H-imidazol-5-yl]ethanone, or a pharmaceutically acceptable salt thereof.

22. The compound of claim 1 which is 9-octadecenoic acid, [4-[4,5-dihydro-1-methyl-5-[methyl(1-oxoheptyl)amino]-4,4-bis(trifluoromethyl)-1H-imidazol-2-yl]phenyl]ester, or a pharmaceutically acceptable salt thereof.

23. The compound of claim 1 which is benzamide, N-[2-(4-cyanophyl)-4,5-dihydro-1-methyl-4,4-bis(trifluoromethyl)-1H-imidazol-5-yl]-4-cyano-N-methyl, or a pharmaceutically acceptable salt thereof.

24. The compound of claim which is benzamide, N-[2-(4-cyanophenyl)-4,5-dihydro-1-methyl-4,4-bis(trifluoromethyl)-1H-imidazol-5-yl]-4-cyano-N-methyl. R-isomer, or a pharmaceutically acceptable salt thereof.

25. The compound of claim 1 which is phenol, 4-[4,5-dihydro-1-methyl-5-[methyl(1-oxoheptyl)amino]-4,4-bis(trifluoromethyl)-1H-imidazol-2-yl]-, acetate (ester), or a pharmaceutically acceptable salt thereof.

26. The compound of claim 1 which is benzamide, N-[2-(4-fluorophenyl)-4,5-dihydro-1-methyl-4,4-bis(trifluoromethyl)-1H-imidazol-5-yl]-4-cyano-N-methyl, or a pharmaceutically acceptable salt thereof.

27. The compound of claim 1 which is benzamide, N-[2-(4-cyanophenyl)-4,5-dihydro-1-methyl-4,4-bis(trifluoromethyl)-1H-imidazol-5-yl]-4-fluoro-N-methyl, or a pharmaceutically acceptable salt thereof.

28. The compound of claim 1 which is benzamide, N-[2-(4-fluorophenyl)-4,5-dihydro-1-methyl-4,4-bis(trifluoromethyl)-1H-imidazol-5-yl]-2,3,4,5,6-pentafluoro-N-methyl, or a pharmaceutically acceptable salt thereof.

29. The compound of claim 1 which is 1-(4-fluorophenyl)-2-[2-(4-fluorophenyl)-4,5-dihydro-1-methyl-4,4-bis(trifluoromethyl)-1H-imidazol-5-yl]-ethanone, or a pharmaceutically acceptable salt thereof.

30. The compound of claim 1 which is 1-(4-fluorophenyl)-2-[2-(4-fluorophenyl)-4,5-dihydro-1-ethyl)-4,4-bis(trifluoromethyl)-1H-imidazol-5-yl]-ethanone, or a pharmaceutically acceptable salt thereof.

31. A pharmaceutical composition comprising an effective ACAT inhibiting or antiatherosclerotic amount of a compound of claim 1 and a pharmaceutically acceptable carrier.

32. A pharmaceutical composition comprising an effective ACAT inhibiting or antiatherosclerotic amount of a compound of claim 2 and a pharmaceutically acceptable carrier.

33. A pharmaceutical composition comprising an effective ACAT inhibiting or antiatherosclerotic amount of a compound of claim 3 and a pharmaceutically acceptable carrier.

34. A pharmaceutical composition comprising an effective ACAT inhibiting or antiatherosclerotic amount of a compound of claim 4 and a pharmaceutically acceptable carrier.

35. A pharmaceutical composition comprising an effective ACAT inhibiting or antiatherosclerotic amount of the compound of claim 5 and a pharmaceutically acceptable carrier.

36. A pharmaceutical composition comprising an effective ACAT inhibiting or antiatherosclerotic amount of the compound of claim 6 and a pharmaceutically acceptable carrier.

37. A pharmaceutical composition comprising an effective ACAT inhibiting or antiatherosclerotic amount of the compound of claim 7 and a pharmaceutically acceptable carrier.

38. A pharmaceutical composition comprising an effective ACAT inhibiting or antiatherosclerotic amount of the compound of claim 8 and a pharmaceutically acceptable carrier.

39. A pharmaceutical composition comprising an effective ACAT inhibiting or antiatherosclerotic amount of the compound of claim 9 and a pharmaceutically acceptable carrier.

40. A pharmaceutical composition comprising an effective ACAT inhibiting or antiatherosclerotic amount of the compound of claim 10 and a pharmaceutically acceptable carrier.

41. A pharmaceutical composition comprising an effective ACAT inhibiting or antiatherosclerotic amount of the compound of claim 11 and a pharmaceutically acceptable carrier.

42. A pharmaceutical composition comprising an effective ACAT inhibiting or antiatherosclerotic amount of the compound of claim 12 and a pharmaceutically acceptable carrier.

43. A pharmaceutical composition comprising an effective ACAT inhibiting or antiatherosclerotic amount of the compound of claim 13 and a pharmaceutically acceptable carrier.

44. A pharmaceutical composition comprising an effective ACAT inhibiting or antiatherosclerotic amount of the compound of claim 14 and a pharmaceutically acceptable carrier.

45. A pharmaceutical composition comprising an effective ACAT inhibiting or antiatherosclerotic amount of the compound of claim 15 and a pharmaceutically acceptable carrier.

46. A pharmaceutical composition comprising an effective ACAT inhibiting or antiatherosclerotic amount of the compound of claim 16 and a pharmaceutically acceptable carrier.

47. A pharmaceutical composition comprising an effective ACAT inhibiting or antiatherosclerotic amount of the compound of claim 17 and a pharmaceutically acceptable carrier.

48. A pharmaceutical composition comprising an effective ACAT inhibiting or antiatherosclerotic amount of the compound of claim 18 and a pharmaceutically acceptable carrier.

49. A pharmaceutical composition comprising an effective ACAT inhibiting or antiatherosclerotic amount of the compound of claim 19 and a pharmaceutically acceptable carrier.

50. A pharmaceutical composition comprising an effective ACAT inhibiting or antiatherosclerotic amount of the compound of claim 20 and a pharmaceutically acceptable carrier.

51. A pharmaceutical composition comprising an effective ACAT inhibiting or antiatherosclerotic amount of the compound of claim 21 and a pharmaceutically acceptable carrier.

52. A pharmaceutical composition comprising an effective ACAT inhibiting or antiatherosclerotic amount of the compound of claim 22 and a pharmaceutically acceptable carrier.

53. A pharmaceutical composition comprising an effective ACAT inhibiting or antiatherosclerotic amount of the compound of claim 23 and a pharmaceutically acceptable carrier.

54. A pharmaceutical composition comprising an effective ACAT inhibiting or antiatherosclerotic amount of the compound of claim 24 and a pharmaceutically acceptable carrier.

55. A pharmaceutical composition comprising an effective ACAT inhibiting or antiatherosclerotic amount of the compound of claim 25 and a pharmaceutically acceptable carrier.

56. A pharmaceutical composition comprising an effective ACAT inhibiting or antiatherosclerotic amount of the compound of claim 26 and a pharmaceutically acceptable carrier.

57. A pharmaceutical composition comprising an effective ACAT inhibiting or antiatherosclerotic amount of the compound of claim 27 and a pharmaceutically acceptable carrier.

58. A pharmaceutical composition comprising an effective ACAT inhibiting or antiatherosclerotic amount of the compound of claim 28 and a pharmaceutically acceptable carrier.

59. A pharmaceutical composition comprising an effective ACAT inhibiting or antiatherosclerotic amount of the compound of claim 29 and a pharmaceutically acceptable carrier.

60. A method of treating hypercholesterolemia or atherosclerosis in a mammal comprising administering to the mammal an effective ACAT inhibiting or antiatherosclerotic amount of a compound of claim 1.

61. A method of treating hypercholesterolemia or atherosclerosis in a mammal comprising administering to the mammal an effective ACAT inhibiting or antiatherosclerotic amount of a compound of claim 2.

62. A method of treating hypercholesterolemia or atherosclerosis in a mammal comprising administering to the mammal an effective ACAT inhibiting or antiatherosclerotic amount of a compound of claim 3.

63. A method of treating hypercholesterolemia or atherosclerosis in a mammal comprising administering to the mammal an effective ACAT inhibiting or antiatherosclerotic amount of a compound of claim 4.

64. A method of treating hypercholesterolemia or atherosclerosis in a mammal comprising administering to the mammal an effective ACAT inhibiting or antiatherosclerotic amount of the compound of claim 5.

65. A method of treating hypercholesterolemia or atherosclerosis in a mammal comprising administering to the mammal an effective ACAT inhibiting or antiatherosclerotic amount of the compound of claim 6.

66. A method of treating hypercholesterolemia or atherosclerosis in a mammal comprising administering to the mammal an effective ACAT inhibiting or antiatherosclerotic amount of the compound of claim 7.

67. A method of treating hypercholesterolemia or atherosclerosis in a mammal comprising administering to the mammal an effective ACAT inhibiting or antiatherosclerotic amount of the compound of claim 8.

68. A method of treating hypercholesterolemia or atherosclerosis in a mammal comprising administering to the mammal an effective ACAT inhibiting or antiatherosclerotic amount of the compound of claim 9.

69. A method of treating hypercholesterolemia or atherosclerosis in a mammal comprising administering to the mammal an effective ACAT inhibiting or antiatherosclerotic amount of the compound of claim 10.

70. A method of treating hypercholesterolemia or atherosclerosis in a mammal comprising administering to the mammal an effective ACAT inhibiting or antiatherosclerotic amount of the compound of claim 11.

71. A method of treating hypercholesterolemia or atherosclerosis in a mammal comprising administering to the mammal an effective ACAT inhibiting or antiatherosclerotic amount of the compound of claim 12.

72. A method of treating hypercholesterolemia or atherosclerosis in a mammal comprising administering to the mammal an effective ACAT inhibiting or antiatherosclerotic amount of the compound of claim 13.

73. A method of treating hypercholesterolemia or atherosclerosis in a mammal comprising administering to the mammal an effective ACAT inhibiting or antiatherosclerotic amount of the compound of claim 14.

74. A method of treating hypercholesterolemia or atherosclerosis in a mammal comprising administering to the mammal an effective ACAT inhibiting or antiatherosclerotic amount of the compound of claim 15.

75. A method of treating hypercholesterolemia or atherosclerosis in a mammal comprising administering to the mammal an effective ACAT inhibiting or antiatherosclerotic amount of the compound of claim 16.

76. A method of treating hypercholesterolemia or atherosclerosis in a mammal comprising administering to the mammal an effective ACAT inhibiting or antiatherosclerotic amount of the compound of claim 17.

77. A method of treating hypercholesterolemia or atherosclerosis in a mammal comprising administering to the mammal an effective ACAT inhibiting or antiatherosclerotic amount of the compound of claim 18.

78. A method of treating hypercholesterolemia or atherosclerosis in a mammal comprising administering to the mammal an effective ACAT inhibiting or antiatherosclerotic amount of the compound of claim 19.

79. A method of treating hypercholesterolemia or atherosclerosis in a mammal comprising administering to the mammal an effective ACAT inhibiting or antiatherosclerotic amount of the compound of claim 20.

80. A method of treating hypercholesterolemia or atherosclerosis in a mammal comprising administering to the mammal an effective ACAT inhibiting or antiatherosclerotic amount of the compound of claim 21.

81. A method of treating hypercholesterolemia or atherosclerosis in a mammal comprising administering to the mammal an effective ACAT inhibiting or antiatherosclerotic amount of the compound of claim 22.

82. A method of treating hypercholesterolemia or atherosclerosis in a mammal comprising administering to the mammal an effective ACAT inhibiting or antiatherosclerotic amount of the compound of claim 23.

83. A method of treating hypercholesterolemia or atherosclerosis in a mammal comprising administering to the mammal an effective ACAT inhibiting or antiatherosclerotic amount of the compound of claim 24.

84. A method of treating hypercholesterolemia or atherosclerosis in a mammal comprising administering to the mammal an effective ACAT inhibiting or antiatherosclerotic amount of the compound of claim 25.

85. A method of treating hypercholesterolemia or atherosclerosis in a mammal comprising administering to the mammal an effective ACAT inhibiting or antiatherosclerotic amount of the compound of claim 26.

86. A method of treating hypercholesterolemia or atherosclerosis in a mammal comprising administering to the mammal an effective ACAT inhibiting or antiatherosclerotic amount of the compound of claim 27.

87. A method of treating hypercholesterolemia or atherosclerosis in a mammal comprising administering to the mammal an effective ACAT inhibiting or antiatherosclerotic amount of the compound of claim 28.

88. A method of treating hypercholesterolemia or atherosclerosis in a mammal comprising administering to the mammal an effective ACAT inhibiting or antiatherosclerotic amount of the compound of claim 29.

89. A crystalline form of the compound of claim 23 which has a melting point of about 131°–134° C.

90. A crystalline form of the compound of claim 23 which has a melting point of about 181°–183° C.

* * * * *